US009333014B2

(12) United States Patent
Gonzalez-Hernandez

(10) Patent No.: US 9,333,014 B2
(45) Date of Patent: May 10, 2016

(54) BONE FIXATION AND REDUCTION APPARATUS AND METHOD FOR FIXATION AND REDUCTION OF A DISTAL BONE FRACTURE AND MALUNION

(71) Applicant: Eduardo Gonzalez-Hernandez, Miami, FL (US)

(72) Inventor: Eduardo Gonzalez-Hernandez, Miami, FL (US)

( * ) Notice: Subject to any disclaimer, the term of this patent is extended or adjusted under 35 U.S.C. 154(b) by 244 days.

(21) Appl. No.: 14/213,310

(22) Filed: Mar. 14, 2014

(65) Prior Publication Data
US 2014/0277177 A1 Sep. 18, 2014

Related U.S. Application Data

(60) Provisional application No. 61/790,849, filed on Mar. 15, 2013, provisional application No. 61/810,384, filed on Apr. 10, 2013.

(51) Int. Cl.
*A61B 17/80* (2006.01)
(52) U.S. Cl.
CPC ......... *A61B 17/8061* (2013.01); *A61B 17/8085* (2013.01); *A61B 17/8014* (2013.01); *A61B 17/8057* (2013.01)
(58) Field of Classification Search
CPC ............... A61B 17/80; A61B 17/8004; A61B 17/8014; A61B 17/8057; A61B 17/8061; A61B 17/8085
See application file for complete search history.

(56) References Cited

U.S. PATENT DOCUMENTS

| 1,950,799 | A | | 3/1934 | Jones |
| 2,500,370 | A | | 3/1950 | McKibbin |
| 2,555,291 | A | | 5/1951 | Poupitch |
| 2,580,821 | A | * | 1/1952 | Nicola ............... A61B 17/8004 322/2 A |
| 2,875,663 | A | | 3/1959 | Wieber |
| 3,489,143 | A | | 1/1970 | Halloran |
| 3,552,389 | A | | 1/1971 | Allgower et al. |
| 3,579,831 | A | | 5/1971 | Stevens et al. |
| 3,716,050 | A | | 2/1973 | Johnston |
| 3,791,380 | A | | 2/1974 | Dawidowski |

(Continued)

FOREIGN PATENT DOCUMENTS

| DE | 86 28 766 U1 | 12/1986 |
| DE | 89 07 443 U1 | 9/1989 |

(Continued)

OTHER PUBLICATIONS

U.S. Appl. No. 10/993,723, filed Nov. 2004, Gonzalez-Hernandez.

(Continued)

*Primary Examiner* — Larry E Waggle, Jr.
(74) *Attorney, Agent, or Firm* — Martin & Ferraro, LLP

(57) ABSTRACT

Apparatus for fixation and reduction of a fractured distal portion of a bone. A bone plate includes an elongated body portion adapted for attachment to a shaft portion of the bone, the body portion defining a longitudinal axis; a head portion connected to the body portion, and projecting therefrom at a first angle with respect to the longitudinal axis, the head portion adapted for attachment to the fractured distal portion of the bone; an alignment tab projecting from the perimeter of one of the head portion in the body portion; and a flex tab connected to a surface of an opening defined in the head portion, the flex tab being pivotable into contact with, and attachable to, the shaft portion of the bone at one of the shaft portion of the bone proximate the fractured distal portion of the bone and the fractured distal portion of the bone.

20 Claims, 16 Drawing Sheets

(56) References Cited

U.S. PATENT DOCUMENTS

| | | | |
|---|---|---|---|
| 3,900,025 A | 8/1975 | Barnes, Jr. | |
| 4,029,091 A * | 6/1977 | von Bezold | A61B 17/80 606/282 |
| 4,263,904 A | 4/1981 | Judet | |
| 4,535,768 A | 8/1985 | Hourahane et al. | |
| 4,683,878 A | 8/1987 | Carter | |
| 4,733,654 A | 3/1988 | Marino | |
| 4,776,330 A | 10/1988 | Chapman et al. | |
| 4,790,302 A | 12/1988 | Colwill et al. | |
| 4,794,919 A | 1/1989 | Nilsson | |
| 4,838,264 A | 6/1989 | Bremer et al. | |
| 4,858,602 A | 8/1989 | Seidel et al. | |
| 4,870,957 A | 10/1989 | Goble et al. | |
| 5,003,969 A | 4/1991 | Azer et al. | |
| 5,015,248 A | 5/1991 | Burstein et al. | |
| 5,041,113 A | 8/1991 | Biedermann et al. | |
| 5,041,114 A | 8/1991 | Chapman et al. | |
| 5,180,383 A | 1/1993 | Haydon | |
| 5,190,544 A | 3/1993 | Chapman et al. | |
| 5,324,291 A | 6/1994 | Ries et al. | |
| 5,356,410 A | 10/1994 | Pennig | |
| 5,364,399 A | 11/1994 | Lowery et al. | |
| 5,423,860 A | 6/1995 | Lizardi et al. | |
| 5,437,667 A | 8/1995 | Papierski et al. | |
| 5,443,516 A | 8/1995 | Albrektsson et al. | |
| 5,458,654 A | 10/1995 | Tepic | |
| 5,462,547 A | 10/1995 | Weigum | |
| 5,472,444 A | 12/1995 | Huebner et al. | |
| 5,505,734 A | 4/1996 | Caniggia et al. | |
| 5,578,035 A | 11/1996 | Lin | |
| 5,584,835 A | 12/1996 | Greenfield | |
| 5,586,985 A | 12/1996 | Putnam et al. | |
| 5,601,553 A | 2/1997 | Trebing et al. | |
| 5,620,449 A | 4/1997 | Faccioli et al. | |
| 5,658,287 A | 8/1997 | Hofmann et al. | |
| 5,665,088 A | 9/1997 | Gil et al. | |
| 5,674,222 A | 10/1997 | Berger et al. | |
| 5,676,667 A | 10/1997 | Hausman | |
| 5,681,311 A | 10/1997 | Foley et al. | |
| 5,709,686 A | 1/1998 | Talos et al. | |
| 5,749,872 A | 5/1998 | Kyle et al. | |
| 5,766,174 A | 6/1998 | Perry | |
| 5,776,194 A | 7/1998 | Mikol et al. | |
| 5,779,704 A | 7/1998 | Kim | |
| 5,785,712 A | 7/1998 | Runciman et al. | |
| 5,840,078 A | 11/1998 | Yerys | |
| 5,868,749 A | 2/1999 | Reed | |
| 5,931,839 A | 8/1999 | Medoff | |
| 5,976,139 A | 11/1999 | Bramlet | |
| 6,030,389 A | 2/2000 | Wagner et al. | |
| 6,096,040 A | 8/2000 | Esser | |
| 6,149,653 A | 11/2000 | Deslauriers | |
| 6,152,927 A | 11/2000 | Farris et al. | |
| 6,200,330 B1 | 3/2001 | Benderev et al. | |
| 6,206,881 B1 | 3/2001 | Frigg et al. | |
| D443,060 S | 5/2001 | Benirschke et al. | |
| 6,270,499 B1 | 8/2001 | Leu et al. | |
| D449,692 S | 10/2001 | Michelson | |
| 6,302,887 B1 | 10/2001 | Spranza et al. | |
| 6,331,179 B1 | 12/2001 | Freid et al. | |
| 6,348,052 B1 | 2/2002 | Sammarco | |
| 6,358,250 B1 | 3/2002 | Orbay | |
| 6,364,881 B1 | 4/2002 | Apgar et al. | |
| 6,364,882 B1 | 4/2002 | Orbay | |
| 6,379,359 B1 | 4/2002 | Dahners | |
| 6,398,783 B1 | 6/2002 | Michelson | |
| 6,406,478 B1 | 6/2002 | Kuo | |
| 6,409,768 B1 | 6/2002 | Tepic et al. | |
| 6,413,259 B1 | 7/2002 | Lyons et al. | |
| 6,440,135 B2 | 8/2002 | Orbay et al. | |
| 6,468,278 B1 | 10/2002 | Muckter | |
| 6,572,620 B1 | 6/2003 | Schon et al. | |
| 6,620,195 B2 | 9/2003 | Goble et al. | |
| 6,623,486 B1 | 9/2003 | Weaver et al. | |
| 6,663,669 B1 | 12/2003 | Reiley | |
| 6,669,701 B2 | 12/2003 | Steiner et al. | |
| 6,695,844 B2 | 2/2004 | Bramlet et al. | |
| 6,706,046 B2 | 3/2004 | Orbay et al. | |
| 6,712,820 B2 | 3/2004 | Orbay | |
| 6,719,759 B2 | 4/2004 | Wagner et al. | |
| 6,730,090 B2 | 5/2004 | Orbay et al. | |
| 6,776,781 B1 | 8/2004 | Uwaydah | |
| 6,863,671 B1 | 3/2005 | Strobel et al. | |
| 6,866,665 B2 | 3/2005 | Orbay | |
| 6,916,323 B2 | 7/2005 | Kitchens | |
| 6,945,973 B2 | 9/2005 | Bray | |
| 7,001,388 B2 | 2/2006 | Orbay et al. | |
| 7,063,701 B2 | 6/2006 | Michelson | |
| 7,128,744 B2 | 10/2006 | Weaver et al. | |
| D536,453 S | 2/2007 | Young et al. | |
| 7,220,246 B2 | 5/2007 | Raulerson et al. | |
| 7,229,445 B2 | 6/2007 | Hayeck et al. | |
| 7,235,079 B2 | 6/2007 | Jensen et al. | |
| 7,354,441 B2 | 4/2008 | Frigg | |
| 7,500,983 B1 | 3/2009 | Kaiser et al. | |
| 7,563,263 B2 | 7/2009 | Orbay et al. | |
| 7,582,107 B2 | 9/2009 | Trail et al. | |
| 7,591,823 B2 | 9/2009 | Tipirneni | |
| 7,604,657 B2 | 10/2009 | Orbay et al. | |
| 7,637,908 B1 | 12/2009 | Gonzalez-Hernandez | |
| 7,651,517 B2 | 1/2010 | Konieczynski et al. | |
| 7,655,029 B2 | 2/2010 | Niederberger et al. | |
| 7,695,472 B2 | 4/2010 | Young | |
| 7,722,653 B2 | 5/2010 | Young et al. | |
| 7,740,648 B2 | 6/2010 | Young et al. | |
| 7,744,638 B2 | 6/2010 | Orbay | |
| 7,776,076 B2 | 8/2010 | Grady, Jr. et al. | |
| 7,780,667 B2 | 8/2010 | Watanabe et al. | |
| 7,780,710 B2 | 8/2010 | Orbay et al. | |
| 7,896,886 B2 | 3/2011 | Orbay et al. | |
| 7,909,859 B2 | 3/2011 | Mosca et al. | |
| 7,914,532 B2 | 3/2011 | Shaver et al. | |
| 7,927,341 B2 | 4/2011 | Orbay et al. | |
| 7,938,850 B2 | 5/2011 | Orbay et al. | |
| 7,951,176 B2 | 5/2011 | Grady et al. | |
| 7,951,178 B2 | 5/2011 | Jensen | |
| 7,955,364 B2 | 6/2011 | Ziolo et al. | |
| D643,121 S | 8/2011 | Milford et al. | |
| D646,785 S | 10/2011 | Milford | |
| 8,062,367 B2 | 11/2011 | Kirschman | |
| 8,100,953 B2 | 1/2012 | White et al. | |
| 8,182,485 B1 | 5/2012 | Gonzalez-Hernandez | |
| 8,361,075 B2 | 1/2013 | Gonzalez-Hernandez | |
| 8,469,999 B2 | 6/2013 | Gonzalez-Hernandez | |
| 8,523,902 B2 | 9/2013 | Heaven et al. | |
| 8,556,946 B2 * | 10/2013 | Prandi | A61B 17/8004 606/286 |
| 8,574,234 B2 | 11/2013 | Gonzalez-Hernandez | |
| 8,597,363 B2 | 12/2013 | Liverneaux et al. | |
| 8,603,091 B2 * | 12/2013 | Lutz | A61B 17/8066 606/281 |
| 8,608,783 B2 * | 12/2013 | Graham | A61B 17/8023 606/280 |
| 8,728,126 B2 | 5/2014 | Steffen | |
| 8,764,808 B2 | 7/2014 | Gonzalez-Hernandez | |
| 2003/0135212 A1 | 7/2003 | Chow | |
| 2003/0135216 A1 | 7/2003 | Sevrain | |
| 2003/0208210 A1 | 11/2003 | Dreyfuss et al. | |
| 2004/0097939 A1 | 5/2004 | Bonutti | |
| 2004/0193278 A1 | 9/2004 | Maroney et al. | |
| 2004/0210220 A1 | 10/2004 | Tornier | |
| 2005/0004574 A1 | 1/2005 | Muckter | |
| 2005/0015089 A1 | 1/2005 | Young et al. | |
| 2005/0021033 A1 | 1/2005 | Zeiler et al. | |
| 2005/0038513 A1 | 2/2005 | Michelson | |
| 2005/0085819 A1 | 4/2005 | Ellis et al. | |
| 2005/0240187 A1 | 10/2005 | Huebner et al. | |
| 2005/0267476 A1 | 12/2005 | Chervitz et al. | |
| 2005/0288681 A1 | 12/2005 | Klotz et al. | |
| 2006/0015072 A1 | 1/2006 | Raulerson | |
| 2006/0015101 A1 | 1/2006 | Warburton et al. | |
| 2006/0161156 A1 | 7/2006 | Orbay | |
| 2006/0217722 A1 | 9/2006 | Dutoit et al. | |
| 2006/0235400 A1 | 10/2006 | Schneider | |

(56) References Cited

U.S. PATENT DOCUMENTS

| | | |
|---|---|---|
| 2006/0241617 A1 | 10/2006 | Holloway et al. |
| 2006/0264947 A1 | 11/2006 | Orbay et al. |
| 2006/0264956 A1 | 11/2006 | Orbay et al. |
| 2006/0271105 A1 | 11/2006 | Foerster et al. |
| 2007/0005074 A1 | 1/2007 | Chudik |
| 2007/0016205 A1 | 1/2007 | Buetter et al. |
| 2007/0083207 A1 | 4/2007 | Ziolo et al. |
| 2007/0123880 A1 | 5/2007 | Medoff |
| 2007/0123885 A1 | 5/2007 | Kirschman |
| 2007/0162015 A1 | 7/2007 | Winquist et al. |
| 2007/0167953 A1 | 7/2007 | Prien et al. |
| 2007/0233114 A1 | 10/2007 | Bouman |
| 2007/0233115 A1 | 10/2007 | Sixto et al. |
| 2008/0015593 A1 | 1/2008 | Pfefferle et al. |
| 2008/0045960 A1 | 2/2008 | Bruecker et al. |
| 2008/0058815 A1 | 3/2008 | Young |
| 2008/0091203 A1 | 4/2008 | Warburton et al. |
| 2008/0132955 A1 | 6/2008 | Frigg |
| 2008/0140130 A1 | 6/2008 | Chan et al. |
| 2008/0154311 A1 | 6/2008 | Staeubli |
| 2008/0161853 A1 | 7/2008 | Arnold et al. |
| 2008/0161860 A1 | 7/2008 | Ahrens et al. |
| 2008/0161863 A1 | 7/2008 | Arnold et al. |
| 2008/0221577 A1 | 9/2008 | Elghazaly |
| 2008/0234749 A1 | 9/2008 | Forstein |
| 2008/0234752 A1 | 9/2008 | Dahners |
| 2008/0249572 A1 | 10/2008 | Tandon |
| 2009/0012571 A1 | 1/2009 | Perrow et al. |
| 2009/0024173 A1 | 1/2009 | Reis, Jr. |
| 2009/0048681 A1 | 2/2009 | Vlachos |
| 2009/0076554 A1 | 3/2009 | Huebner et al. |
| 2009/0105838 A1 | 4/2009 | Russo et al. |
| 2009/0171399 A1 | 7/2009 | White et al. |
| 2009/0192550 A1 | 7/2009 | Leung et al. |
| 2009/0216270 A1 | 8/2009 | Humphrey |
| 2009/0228010 A1 | 9/2009 | Gonzalez-Hernandez et al. |
| 2009/0254089 A1 | 10/2009 | Tipirneni et al. |
| 2009/0254189 A1 | 10/2009 | Scheker |
| 2009/0264936 A1 | 10/2009 | Gonzalez-Hernandez et al. |
| 2009/0275987 A1 | 11/2009 | Graham et al. |
| 2009/0275991 A1 | 11/2009 | Medoff |
| 2009/0281578 A1 | 11/2009 | Spencer |
| 2009/0299369 A1 | 12/2009 | Orbay et al. |
| 2009/0306711 A1 | 12/2009 | Stone et al. |
| 2009/0312760 A1 | 12/2009 | Forstein et al. |
| 2009/0312802 A1 | 12/2009 | Dasilva |
| 2009/0326591 A1 | 12/2009 | Spencer, Jr. |
| 2010/0030276 A1 | 2/2010 | Huebner et al. |
| 2010/0057086 A1 | 3/2010 | Price et al. |
| 2010/0145339 A1 | 6/2010 | Steffen |
| 2010/0198258 A1 | 8/2010 | Heaven et al. |
| 2010/0217393 A1 | 8/2010 | Theofilos |
| 2010/0262194 A1 | 10/2010 | Wagner et al. |
| 2010/0324602 A1 | 12/2010 | Huebner et al. |
| 2010/0331844 A1 | 12/2010 | Ellis et al. |
| 2011/0152943 A1 | 6/2011 | Gonzalez-Hernandez |
| 2011/0295324 A1* | 12/2011 | Donley ............... A61B 17/8061 606/289 |
| 2012/0083848 A1 | 4/2012 | Gonzalez-Hernandez |
| 2012/0109322 A1 | 5/2012 | Gonzalez-Hernandez |
| 2012/0197308 A1 | 8/2012 | Gonzalez-Hernandez |
| 2012/0226321 A1 | 9/2012 | Gonzalez-Hernandez |
| 2012/0226322 A1 | 9/2012 | Gonzalez-Hernandez |
| 2012/0226323 A1 | 9/2012 | Gonzalez-Hernandez |
| 2013/0096629 A1 | 4/2013 | Rollinghoff et al. |
| 2013/0116734 A1 | 5/2013 | Gonzalez-Hernandez |
| 2013/0289627 A1 | 10/2013 | Gonzalez-Hernandez |
| 2014/0121709 A1 | 5/2014 | Gonzalez-Hernandez |
| 2014/0121779 A1 | 5/2014 | Gonzalez-Hernandez |

FOREIGN PATENT DOCUMENTS

| | | |
|---|---|---|
| DE | 92 00 328 U1 | 2/1992 |
| DE | 43 43 117 A1 | 6/1995 |
| DE | 198 57 279 A1 | 6/2000 |
| DE | 299 07 161 U1 | 8/2000 |
| EP | 0 551 588 A1 | 11/1992 |
| EP | 1 132 052 A2 | 9/2001 |
| EP | 1 468 655 A2 | 10/2004 |
| FR | 2 606 268 A1 | 5/1988 |
| FR | 2 680 673 A1 | 3/1993 |
| JP | 4-138152 A | 5/1992 |
| WO | WO 99/38448 A1 | 8/1999 |
| WO | WO 2005/037117 A1 | 4/2005 |
| WO | WO 2008/007194 A2 | 1/2008 |
| WO | WO 2008/007196 A2 | 1/2008 |
| WO | WO 2012/003884 | 1/2012 |

OTHER PUBLICATIONS

U.S. Appl. No. 11/079,350, filed Mar. 2005, Gonzalez-Hernandez.
U.S. Appl. No. 11/366,676, filed Mar. 2006, Gonzalez-Hernandez.
U.S. Appl. No. 11/493,122, filed Jul. 2006, Gonzalez-Hernandez.
U.S. Appl. No. 11/526,331, filed Sep. 2006, Gonzalez-Hernandez.
U.S. Appl. No. 11/707,775, filed Feb. 2007, Gonzalez-Hernandez.
U.S. Appl. No. 13/663,129, filed Oct. 2012, Gonzalez-Hernandez.
U.S. Appl. No. 13/663,209, filed Oct. 2012, Gonzalez-Hernandez.
U.S. Appl. No. 13/840,194, filed Mar. 2013, Gonzalez-Hernandez.
U.S. Appl. No. 14/189,681, Gonzalez-Hernandez.
Acumed; ACU-LOC Wrist Plating System; Jul. 2009; 20 pages.
Acumed; The Mayo Clinic Congruent Elbow Plates (catalog); 2003; 19 pages.
Acumed; The Mayo Clinic Congruent Elbow Plate System (catalog); Apr. 2006; 20 pages.
Christie, J., C.R. Howie and P.C. Armour, Fixation of displaced subcapital femoral fractures. Compression screw fixation versus double divergent pins. *J Bone Joint Surg [Br]* 1988; 70-B: 199-201.
Cross, W.M. et al., "Achieving stable fixation: biomechanical designs for fracture healing," AAOS Now (2008) 3 pages.
Guha, AR, et al.; "A New Technique of Fixation of Radial Head Fractures Using a Modified Tubular Plate," Journal of Postgraduate Medicine; Jul. 2004; vol. 50, Issue 2; pp. 113-114; Accessed Aug. 6, 2008 at: http://www.jpgmonline.com/articie.asp?issn=0022-3859; year=2004;volume=50;issue=2;spage=113;epage=114;aulast= Guha.
Hand Innovations, LLC; DVR Anatomic, Volar Plating System; 2007; 4 pages.
Hussain M., R.N. Natarajan, A.H. Fayyazi, B.R. Braaksma, G.B. Andersson and H.S. An, *Screw angulation affects bone-screw stresses and bone graft load sharing in an anterior cervical corpectomy fusion with a rigid screw-plate construct: a finite element model study*; Spine Journal, vol. 9, Issue 12; Dec. 2009; pp. 1016-1023 (published online Oct. 12, 2009).
Lakatos, R. et al.; "General principles of internal fixation"; eMedicine; Aug. 2006; 51 pages.
"MIS Technique," published by Zimmer®, 1 page, prior to Nov. 19, 2004.
Postak, Paul D.; "Biomechanical Properties of Fixed-Angle Volar Distal Radius Plates Under Dynamic Loading;" 2007; 6 pages.
Robert, III, K.Q., R. Chandler, R,V, Barratta, K.A. Thomas and M.B. Harris, The effect of divergent screw placement on the initial strength of plate-to-bone fixation. *J Trauma*. Dec. 2003;55(6):1139-44.
Synthes, "Large Fragment LCP Instrument and Implant Set;" technique guide; 2003; 31 pages.
Synthes; 3.5 mm LCP Periarticular Proximal Humerus Plate; Apr. 2010; 22 pages.
Synthes; Locking Compression Plate (LCP) System (brochure); 2003; 6 pages.
Synthes, "Locking Compression Plate (LCP) System. Locking screw technology and conventional plating in one system;" 2003; 6 pages.
Synthes; Locking Compression Plate (LCP) System (brochure); Jan. 2007; 6 pages.
Synthes; Modular Mini Fragment LCP System (brochure); 2007; 12 pages.
Synthes; Small Fragment Locking Compression Plate (LCP) System (brochure); 2002; 43 pages.
Written Opinion of the International Searching Authority; International Application No. PCT/US2009/036211; Sep. 23, 2010; 8 pages.

(56) References Cited

OTHER PUBLICATIONS

"Zimmer® Universal Locking System," The Journal of Bone and Joint Surgery, vol. 89, No. 7, Jul. 2007, 1 page.

Zimmer, Inc. "Zimmer® Universal Locking System," brochure (2006), 4 pages.

Zimmer, Inc.; "Zimmer Universal Locking System;" brochure; 2009, 2 pages.

Zimmer, Inc. "Zimmer Holdings to Launch Innovative Locking Plate System at Orthopaedic Trauma Association Meeting," Sep. 14, 2006; 3 pages.

Zimmer, Inc.; "Zimmer Small Fragment Universal Locking System;" Surgical Technique; 2010; 16 pages.

Zimmer; Zimmer Periarticular Plating System-Low-Profile Fixation (catalog); 2003; 8 pages.

\* cited by examiner

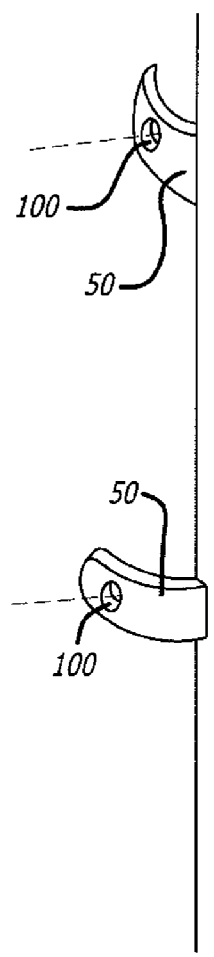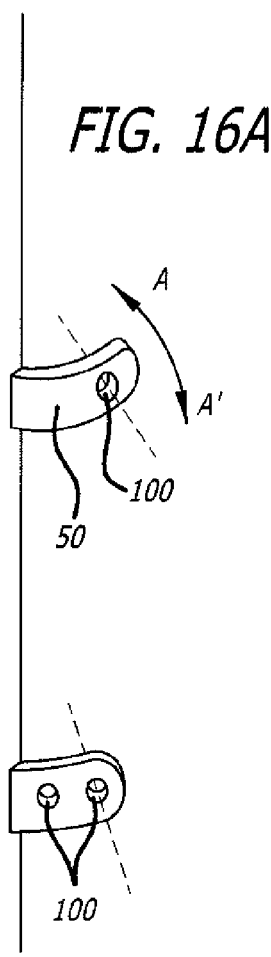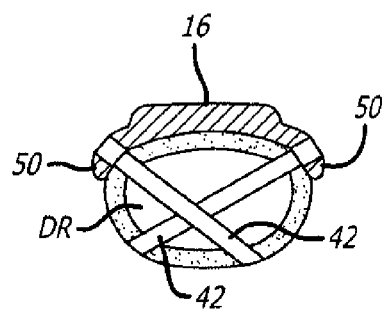
FIG. 16A
FIG. 16B
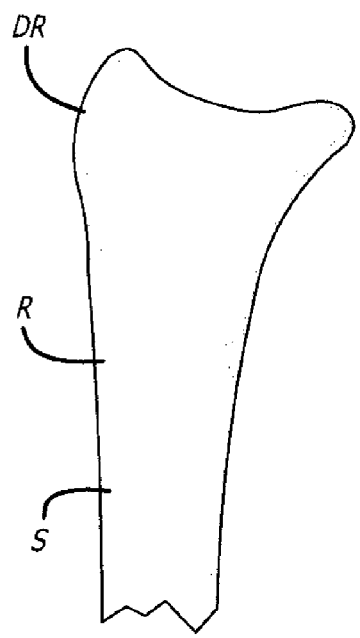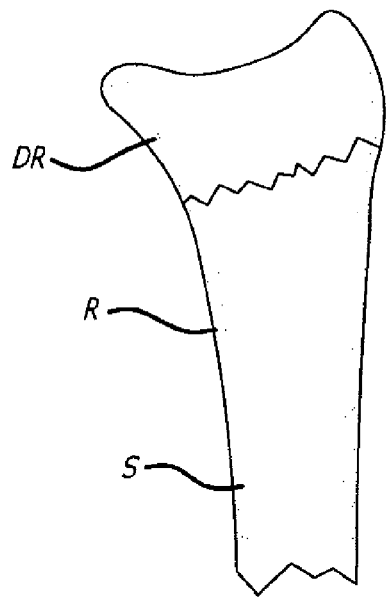
FIG. 17
FIG. 18

US 9,333,014 B2

BONE FIXATION AND REDUCTION APPARATUS AND METHOD FOR FIXATION AND REDUCTION OF A DISTAL BONE FRACTURE AND MALUNION

The present application claims the benefit of U.S. Provisional Application No. 61/790,849, filed Mar. 15, 2013 and U.S. Provisional Application No. 61/810,384, filed Apr. 10, 2013; all of which are incorporated by reference herein.

FIELD OF THE INVENTION

The present invention relates to a distal bone fracture fixation and reduction apparatus and a method for fixation and reduction of a distal bone fracture, and more particularly to a distal bone fracture fixation and reduction apparatus and method using a bone plate with a flex tab for distal radius fracture fixation and reduction, and for distal radius malunion fixation and reduction.

DESCRIPTION OF THE PRIOR ART

The use of bone plates for fixation and reduction of fractures and malunions of distal portions of bones, for example fractures and malunions of the distal radius are known. A fixation and reduction apparatus and method is needed to bring the distal fracture fragment of the bone in suitable alignment with the proximal fracture fragment of the bone shaft, and to fix the bone fragments together. Traditional bone plates, however, are difficult to use for this purpose, because it is extremely difficult for a surgeon, to hold the bone fracture fragments and the bone plate together with one hand while attempting to attach the bone plate to the bone with a drill or other surgical tool held in his other hand. Traditional bone plates, in addition, are particularly inadequate for use in fixation and reduction of comminuted fractures of distal ends of bones, because with such a compound fracture there are more fractured bone fragments for the surgeon to attempt to hold together with the bone plate in one hand, while attempting to hold the drill or other surgical tool in his other hand. The above-described shortcomings with traditional bone plates are particularly well-known when such bone plates are attempted to be used, e.g., with a fractured or malformed distal radius, a fractured or malformed distal tibia, a fractured or malformed distal femur, a fractured or malformed proximal humerus, a fractured or malformed metacarpal, or a fractured or malformed phalange.

FIGS. 19-20 depict shortcomings of attempting to reduce a distal bone fracture or malunion using the above-described traditional bone plates and methods. FIG. 17 is a sagittal view of a distal radius contour. FIG. 18 depicts a distal radius which has sustained a fracture, with dorsal angulation of the distal fragment. FIG. 19 depicts a traditional method wherein a surgeon's hands are occupied performing a very difficult, and at times impossible balancing act of attempting to hold two fractured distal bone fragments in alignment along with a bone plate with one hand, while attempting to hold a drill or other surgical tool with the other hand. FIG. 20 depicts an incomplete reduction, after the traditional plate has been attacted to the distal bone fracture, with a distal fastener penetrating the joint. This penetration by the fastener can cause pain and obstruction to subsequent motion of the joint. Moreover, because the distal fracture fragment is not well reduced, it can erode, which can result in further damage to adjacent tendons.

SUMMARY OF THE INVENTION

Accordingly, the present invention the present invention is directed to a bone fixation and reduction apparatus and method for fixation and reduction of a distal bone fracture and malunion, which substantially obviates one or more of the problems caused by the limitations and disadvantages of the related art.

An apparatus for fixation and reduction of a fractured distal portion of a bone includes a bone plate. The bone plate, as broadly embodied herein, includes an elongated body portion adapted for attachment to a shaft portion of the bone, the elongated body portion defining a longitudinal axis extending substantially parallel to the shaft portion of the bone; a head portion connected to the elongated body portion, and projecting from the elongated body portion at a first angle with respect to the longitudinal axis, the head portion being adapted for attachment to the fractured distal portion of the bone; at least one alignment tab projecting from a perimeter of at least one of the head portion and the elongated body portion; and a flex tab connected to a surface of an opening defined in the head portion and extending substantially parallel to the longitudinal axis, adapted to be pivoted into contact with, and to be attached to, at least one of the shaft portion of the bone proximate the fractured distal portion of the bone and the fractured distal portion of the bone.

Preferably, the apparatus further includes at least one fastener adapted to be inserted through at least one aperture defined in the elongated body portion for attaching the elongated body portion to the shaft portion of the bone. At least one aperture can be a bidirectional aperture adapted to receive two fasteners therethrough. The apparatus further includes at least one fastener adapted to be inserted through at least one aperture defined in the head portion for attaching the head portion to the distal portion of the bone. The apparatus further includes at least one fastener adapted to be inserted through an aperture defined in the flex tab for attaching the flex tab to the at least one of the shaft portion of the bone proximate the distal portion of the bone and the fractured distal portion of the bone.

Preferably, at least one of the at least one alignment tab projecting from the perimeter of at least one of the head portion and the elongated body portion is adapted for positioning the bone plate on the bone. It is further preferred that at least one of the at least one alignment tab projecting from the perimeter of the head portion has a first aperture defined therein adapted to receive therethrough a first fastener in a first line in a plane substantially perpendicular to the longitudinal axis, the first line extending from the first aperture to a center of the distal portion of the bone. It is further preferred that a second alignment tab projecting from the perimeter of the head portion has a second aperture defined therein adapted to receive therethrough a second fastener in a second line, in the plane substantially perpendicular to the longitudinal axis, the second line extending from the second aperture through the center of the distal portion of the bone, and crossing the first line. It is further preferred that at least on third fastener be inserted through at least one aperture in the head portion of the bone plate in at least one third line through the center of the bone and crossing at least one of the first line and the second line. The crossing configuration of the screws along these lines can result in fixation and reduction of a comminuted fracture of the fractured distal portion of the bone. The alignment tabs are flexible through a range of acute angles prior to attachment to the bone, and serve the above-described dual function of positioning the bone plate on the bone, and fixating/reducing a comminuted fracture of the fractured distal portion of the bone.

Preferably, the flex tab, after attachment to the at least one of the surface of the elongated shaft portion proximate the fractured distal portion of the bone and the fractured distal portion of the bone, is adapted to stabilize the bone plate with respect to the bone.

As broadly embodied herein, the apparatus for fixation and reduction of a fractured distal portion of a bone, is adapted for fixation and reduction of at least one of a fractured distal radius, a fractured distal tibia, a fractured distal femur, a fractured proximal humerus, a fractured metacarpal, a fractured proximal phalange, a malunion of a distal radius, a malunion of a distal tibia, a malunion of the distal femur, a malunion of the proximal humerus, a malunion of a metacarpal, and a malunion of a proximal phalange.

A method for fixation and reduction of fractional distal portion of a bone, such as a fractured distal portion of a radius, includes utilizing a bone plate including: an elongated body portion adapted for attachment to a shaft portion of the bone, the elongated body portion defining a longitudinal axis extending substantially parallel to the shaft portion of the bone; a head portion connected to the elongated body portion, and projecting therefrom at a first angle with respect to the longitudinal axis, the head portion being adapted for attachment to the fractured distal portion of the bone; at least one alignment tab projecting from a perimeter of at least one of the head portion and the elongated body portion; and a flex tab connected to a surface of an opening defined in the head portion extending substantially parallel to the longitudinal axis, adapted to be pivoted into contact with, and to be attached to, at least one of the shaft portion of the bone proximate the fractured distal portion of the bone and the fractured distal portion of the bone; aligning the head portion on the fractured distal portion of the bone, such that the elongated body portion projects away from the shaft portion of the bone at an angle corresponding to the first angle; pivoting the flex tab into contact with at least one of the shaft portion of the bone proximate the fractured distal portion of the bone and the fractured distal portion of the bone; attaching the flex tab to the at least one of the shaft portion of the bone proximate the fractured distal portion of the bone and the fractured distal portion of the bone; attaching the at least one alignment tab to the bone; attaching the head portion to the fractured distal portion of the bone; applying pressure to the elongated body portion to bring the elongated body portion into contact with the shaft portion of the bone; and attaching the elongated body portion to the shaft portion of the bone.

Applying pressure to the elongated body portion moves the fractured distal portion of the bone into alignment with the shaft portion of the bone.

Attaching the flex tab to the at least one of the shaft portion proximate the fractured distal portion of the bone and the fractured distal portion of the bone stabilizes the bone plate with respect to the bone.

Attaching the at least one alignment tab projecting from at least one of the head portion and the elongated body portion performs the functions of positioning the bone plate on the bone, and attaching the bone plate to the bone. Furthermore inserting a first fastener through a first aperture defined in a first alignment tab projecting from the head portion, in a first line, in a plane substantially perpendicular to the longitudinal axis, the first line extending from the at least one aperture to a center of the fractured distal portion of the bone can perform an additional function of attaching together comminuted fractured portions of the fractured distal portion of the bone. Attaching together the comminuted fractured portions of the fractured distal portion of the bone can further be achieved by inserting a second fastener through a second aperture defined in a second alignment tab of the at least one alignment tab projecting from the head portion, in a second line in the plane substantially perpendicular to the longitudinal axis, the second line extending from the second alignment tab to the center of the fractured distal portion of the bone, and crossing the first line. Attaching together the comminuted fractured portions of the fractured distal portion of the bone can further be achieved by inserting at least one third fastener through at least one third aperture defined in the head portion, in at least one third line in the plane substantially perpendicular to the longitudinal axis, extending from the head portion to the center of the fractured distal portion of the bone, and crossing at least one of the first line and the second line.

A method for fixation and reduction of a malformed distal portion of a bone, such as a malformed distal radius, includes: utilizing a bone plate including an elongated body portion adapted for attachment to a shaft portion of the bone, the elongated body portion defining a longitudinal axis extending substantially parallel to a shaft portion of the bone; a head portion connected to the elongated body portion, and projecting therefrom at a first angle with respect to the first longitudinal axis, the head portion being adapted for attachment to the fractured distal portion of the bone; at least one alignment tab projecting from a perimeter of at least one of the head portion and the elongated body portion; and a flex tab connected to a surface of an opening defined in the head portion and extending substantially parallel to the longitudinal axis, adapted to be pivoted into contact with, and to be attached to, at least one of the shaft portion of the bone proximate the malformed distal portion of the bone and the malformed distal portion of the bone; cutting the malformed distal portion of the bone with respect to the shaft portion of the bone proximate the malformed distal portion of the bone; aligning the head portion on the malformed distal portion of the bone, such that said elongated body portion projects away from the shaft portion of the bone at an angle corresponding to the first angle; pivoting the flex tab into contact with the at least one of the shaft portion of the bone proximate the malformed distal portion of the bone and the malformed distal portion of the bone; attaching the flex tab to the at least one of the shaft portion of the bone proximate the malformed distal portion of the bone and the malformed distal portion of the bone; attaching the at least one alignment tab to the bone; attaching the head portion to the malformed distal portion of the bone, such that the elongated body portion projects away from the shaft portion of the bone and an angle corresponding to the first angle; applying pressure to the elongated body portion to bring the elongated body portion into contact with the shaft portion of the bone; and attaching the elongated body portion to the shaft portion of the bone.

Additional objects and advantages of the present invention will be set forth in the description which follows, and in part will be apparent from review of the following specification and the accompanying drawings, or may be learned by practice of the invention.

BRIEF DESCRIPTION OF THE DRAWINGS

The accompanying drawings, which are Incorporated in and constitute a part of the specification, illustrate preferred embodiments of the invention and, together with the description, serve to explain the objects, advantages, and principles of the invention. In the drawings:

FIG. 16A is a front perspective view of the elongated aperture portion of the bone fixation and reduction apparatus in accordance with the invention, depicting arcs of travel of the respective adjustable alignment tabs through a range of acute angles;

FIG. 16B is a cross-sectional view viewed from above of the head portion of the bone fixation and reduction apparatus in accordance with the invention attached to the fractured distal radius, with the alignment tabs projecting from the perimeter of the head portion pivoted into contact with the distal radius, and fasteners extending in crossing lines through the center of distal radius to attach together comminuted fractured portions of a comminuted fractured distal radius;

FIG. 17 is a side perspective view of a radius and a distal radius;

FIG. 18 is a distal radius contour depicted from a sagittal view;

DETAILED DESCRIPTION OF THE PREFERRED EMBODIMENT

Figure 1:
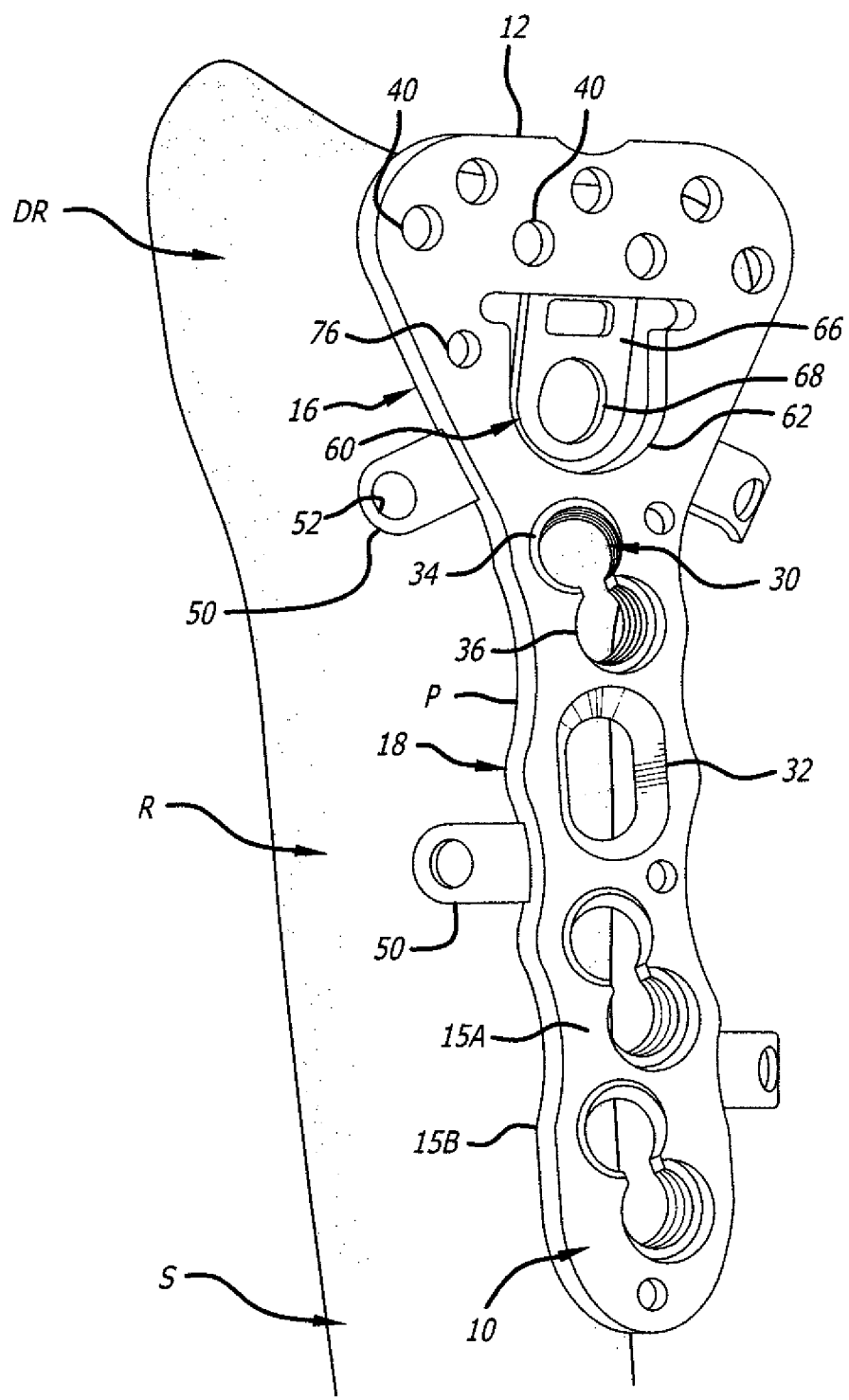
FIG. 1 is a front perspective view of a bone fixation and reduction apparatus in accordance with the invention, aligned for attachment to a radius and a distal radius.

Reference will now be made in detail to the present preferred embodiments of the invention, examples of which are illustrated in the accompanying drawings. Whenever possible, the same reference numbers will be used throughout the drawings to refer to the same or like parts.

The bone plate of the present invention is generally indicated by the numeral 10 in FIGS. 1-16B. While the bone plate 10 is depicted in FIGS. 1-16B in use with respect to reducing and repairing a fractured distal radius DR, the bone plate 10 is not limited thereto. In addition to use with a radius R, the bone plate 10 can be used elsewhere in the body to facilitate reduction and repair of a bone fracture. For example, and without limitation, the bone plate 10 in accordance with the invention can be used in the fixation and reduction of a fracture or malunion of a distal tibia, a distal femur, a proximal humerus, a metacarpal, and a proximal phalange.

The bone plate 10 includes a first end 12 and a second end 14, an upper surface 15A, a lower surface 15B, and a length extending between the first and second ends 12 and 14. The lower surface 15B serves in engaging various portions of the radius R. As depicted at least in FIG. 1, the bone plate 10 includes a head portion 16 and a body portion 18. The upper and lower surfaces 15A and 15B extend along both of the head portion 16 and the body portion 18. Furthermore, the head portion 16 extends from the first end 12 toward the body portion 18, and the body portion 18 extends from the second end 14 toward the head portion 16.

The body portion 18 is elongated, and includes various apertures for receiving fasteners (such as fasteners 20, 22, 24, and 26 depicted in at least FIG. 11) therethrough to attach the bone plate 10 to portions of the radius R. More specifically, the various apertures formed in the body portion 18 can, for example, be used in attaching the bone plate 10 to portions of the radial shaft S and/or the fractured distal radius DR. As discussed below, the fasteners 20, 22, 24, and 26 can have various shapes and sizes.

The apertures provided in the body portion 18 can include bi-directional apertures 30 and elongated apertures 32. The bi-directional apertures 30 are configured to receive a fastener (such as one of the fasteners 22, 24, and 26) in a first fastener receiving portion 34, and configured to receive another fastener (such as one of the fasteners 22, 24, and 26) in a second fastener receiving portion 36. As such, the bi-direction apertures 30 can each accommodate receipt of two fasteners therein. The first and second fastener receiving portions 34 and 36 can be oriented at different angles such that, when fasteners are received therein, the fasteners are oriented in different directions relative to one another. Similar bi-direction apertures for use with bone plates are disclosed in U.S. Publication No. 2012/0197308, which is incorporated by reference herein. The elongated aperture 32 is configured to receive a fastener (such as the fastener 20) therein. When the fastener 20 is inserted through the elongated aperture 32 and into the radius R, the elongation of the elongated aperture 32 allows the bone plate 10 to be adjusted therealong relative to the radius R (and the fastener received therein).

As depicted in at least FIG. 1, the head portion 16 expands in width along the length of the bone plate 10 from the body portion 18 to the first end 12. The head portion 16 includes various apertures 40 for receiving fasteners (such as fasteners 42 depicted in at least FIG. 10) therethrough to attach the bone plate 10 to portions of the radius R. More specifically, the apertures 40 can, for example, be used to attach the bone plate 10 to portions of the fractured distal radius DR. As discussed below, the fasteners 42 can have various shapes and sizes. The apertures 40 can be oriented at different angles such that, when the fasteners 42 are received therein (as depicted at least in FIG. 10), the fasteners 42 are oriented in different directions relative to one another.

Alignment tabs (or fixation legs) 50 can be provided at different locations along the perimeter P of the bone plate 10. For example, as depicted at least in FIG. 1, two of the alignment tabs 50 are provided along the perimeter P on opposite sides of the head portion 16, and two of the alignment tabs 50 are provided along the perimeter P on opposite sides of the body portion 18. The alignment tabs 50 formed on the perimeter P at the head portion 16 are located in the same position relative to the length of the bone plate 10. The alignment tabs 50 formed on the perimeter P at the body portion 18 are staggered at different positions relative to the length of the bone plate 10.

The alignment tabs 50 depend downwardly from the perimeter P and can be used in positioning the bone plate 10 relative to the radius R. More specifically, the alignment tabs 50 can serve in guiding the bone plate 10 into position relative to the radius R. Additionally, the alignment tabs 50 can each include an aperture 52 formed therethrough for receiving a fastener (such as one of the fasteners 42 therein). Thus, in addition to fasteners received in apertures 30, 32, and 40, fasteners received in the apertures 52 can be used in attaching the bone plate 10 the radius R. In addition to their alignment and attachment functions, the alignment tabs 50 projecting from the head portion 16 also can be used to attach together comminuted fracture portions of a comminuted fracture of the distal radius. For example, as depicted in FIG. 16A, a first fastener 42 can be inserted through a first aperture 52 defined in a first alignment tab 50 projecting from the head portion 16 in a first line extending through a center portion of the fractured distal radius DR. If desired, a second fastener 42 can be inserted through an aperture 52 in a second alignment tab 50 in a second line extending through the center of the fractured distal radius DR, the second line crossing the first line. If further desired, at least one third fastener 42 can be inserted through at least one aperture 40 in the head portion 16 in at least one third line through the center of the fractured distal radius, the third line crossing at least one of the first line and the second line. In this arrangement, tightening of the various fasteners inserted through the various apertures will compress the alignment tabs 50 and the head portion 16 together, while simultaneously drawing together the comminuted fractured portions of the fractured distal radius.

A flex tab 60 can also be used in facilitating reduction and repair of the fractured distal radius DR. The flex tab 60 extends downwardly (as depicted at least in FIG. 2) from a portion of the lower surface 15B at the head portion 16. The flex tab 60 is integrally attached to the head portion 16. The flex tab 60 can be formed from a portion of the head portion 16 by, for example, pressing or stamping operations, or can be attached to the head portion 16 via, for example, brazing or welding operations.

As depicted at least in FIG. 1, the flex tab 60 is provided adjacent an opening 62. The dimensions of the opening 62 are larger than the flex tab 60 to accommodate flexure of the flex tab 60 into and out of the opening 62. The flex tab 60 includes a first surface 64 and an opposite second surface 66. Like the lower surface 15B of the bone plate 10, the first surface 64 is oriented downwardly.

When pressure is applied to the second surface 66 of the flex tab 60, the flex tab 60 bends into the opening 62, and when pressure is removed from the second surface 66 of the flex tab 60 bends out of the opening 62. As such, the flex tab 60 is configured to resist flexure thereof into the opening 62. Thus, when the bone plate 10 is being applied to the radius R (see e.g., FIGS. 3-8) the flex tab 60 serves to exert pressure on a portion of the fractured distal radius DR, and when the plate 10 is attached to the radius R (see e.g., FIGS. 9-15), the flex tab 60 continues to exert pressure on the portion or portions of the fractured distal radius DR. The pressure applied by the flex tab 60 can be used in forcing or maintaining a portion or portions of the fractured distal radius DR in position relative to the remainder of the fractured distal radius DR. In addition, when the bone plate 10 is being applied to the fractured distal radius DR, the flex tab 60 can be attached to the shaft S of the radius R proximate the distal radius DR, thereby applying pressure to the shaft S of the radius R and stabilizing the bone plate 10 relative to the shaft S of the radius R and relative to the distal radius DR.

The flex tab 60 can include an aperture 68 formed therethrough for receiving a fastener (not shown) for insertion into the fractured distal radius DR or into the shaft S of the radius R proximate the distal radius DR. The fastener received in the aperture 68 can be used in attaching the flex tab 60 to a portion or portions of the fractured distal radius DR or into the shaft S of the radius R proximate the fractured distal radius DR. When fasteners are received in the apertures 42 of the head portion 16 and in the aperture 68 of the flex tab 60, the bone plate 10 can be used as a lever to bring a portion or portions of the fractured distal radius into alignment with the remainder of the fractured distal radius. That is, when the head portion 16 is attached to at least one fragment of the fractured distal radius DR, and the flex tab 60 is attached to a portion of the fractured distal radius DR still attached to the radial shaft S, the bone plate 10 can be used as a lever to bring the at least one fragment into alignment with the portion of the fractured distal radius DR still attached to the radial shaft S (see FIGS. 8 and 9 of Attachment A). In doing so, the body portion 18 effectively serves as a handle to aid in prying of the at least one fragment into position.

Figure 9:
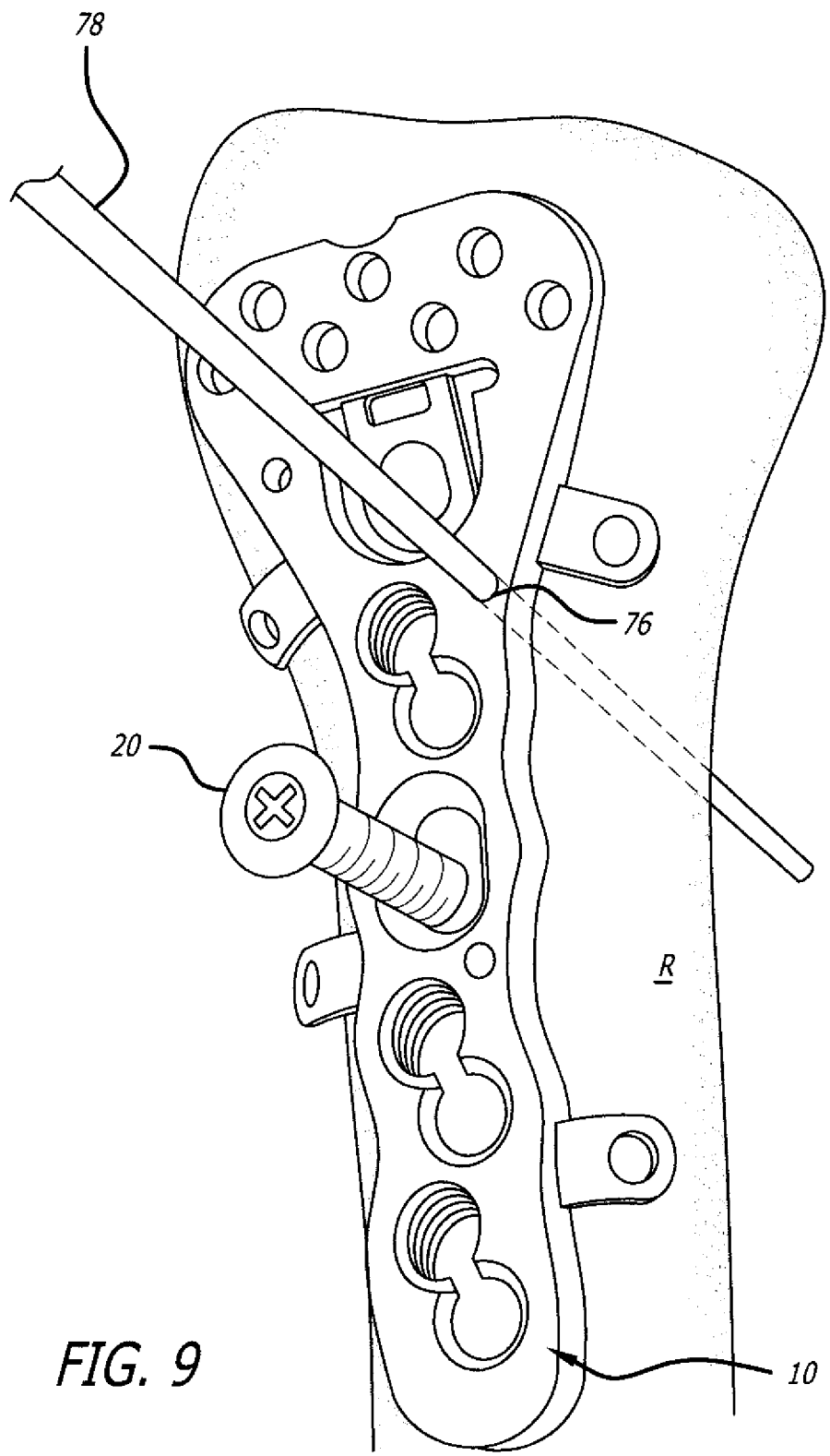
FIG. 9 is a front perspective view of the bone fixation and reduction apparatus as depicted in FIG. 6; viewed from an opposite perspective, and depicting an adjusting fastener inserted through an elongated aperture for adjusting a position of the bone fixation and reduction apparatus with respect to the radius, and a surgical pin for temporarily placing the bone fixation and reduction apparatus on the radius.

Apertures 76 for receiving surgical pins 78 can also be provided in the head portion 16 and the body portion 18. As depicted in FIG. 9, receipt of one of the surgical pins 78 in one of the apertures 76 affords temporary placement of the bone plate 10 relative to the radius R. Thereafter, fasteners (such as the fasteners 20, 22, 24, 26, and 42) can be received through the apertures 30, 32, 40, and 52 to attach the bone plate 10 to the radius R.

As discussed above, the fasteners 20, 22, 24, 26, and 42 can have various shapes and sizes. For example, the heads and shafts of the fasteners 20, 22, 24, 26, and 42 can have various lengths and have different sizes and shapes (e.g., be configured to have cylindrical or frusto-conical shaped head portions). The heads can be provided with or without threads facilitating engagement with complimentary structures provided in the corresponding apertures of the bone plate 10. Furthermore, the shafts can be provided with regular roughened or rough surfaces (hereinafter regular roughened surfaces), irregular roughened or rough surfaces (hereinafter irregular roughened surfaces), and/or smoothened or smooth surfaces (hereinafter smoothened surfaces). The regular roughened surfaces are repeating patterns of surface protrusions or indentations (such as threads, ratchets, or similar structures), and the irregular roughened surfaces (such as barbs or similar structures) are non-repeating surface protrusions or indentations. The surfaces of the shafts can serve in preventing withdrawal of the fasteners from the portion of the radius R. Furthermore, the fasteners 20, 22, 24, 26, and 42 can also include the features of fasteners disclosed in U.S. Publication No. 2012/0197308.

Figure 2:
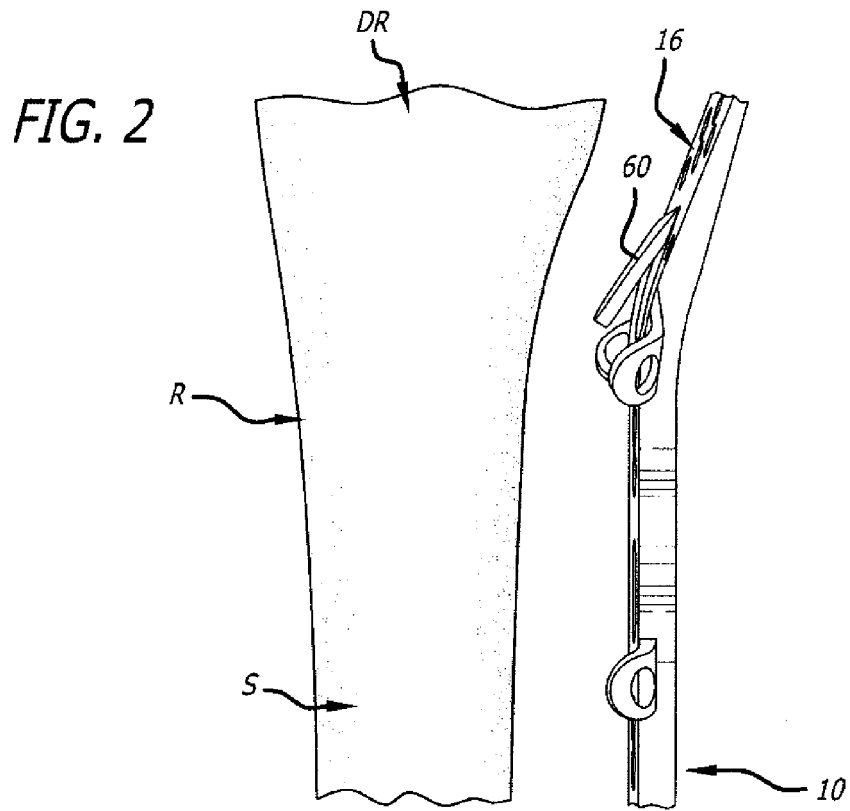
FIG. 2 is a side view of the bone fixation and reduction apparatus as depicted in FIG. 1, aligned for attachment to the radius and the distal radius with a flex tab being pivoted toward at least one of a shaft of the radius proximate the fractured distal radius and the fractured distal radius, in accordance with the invention.
Figure 3:
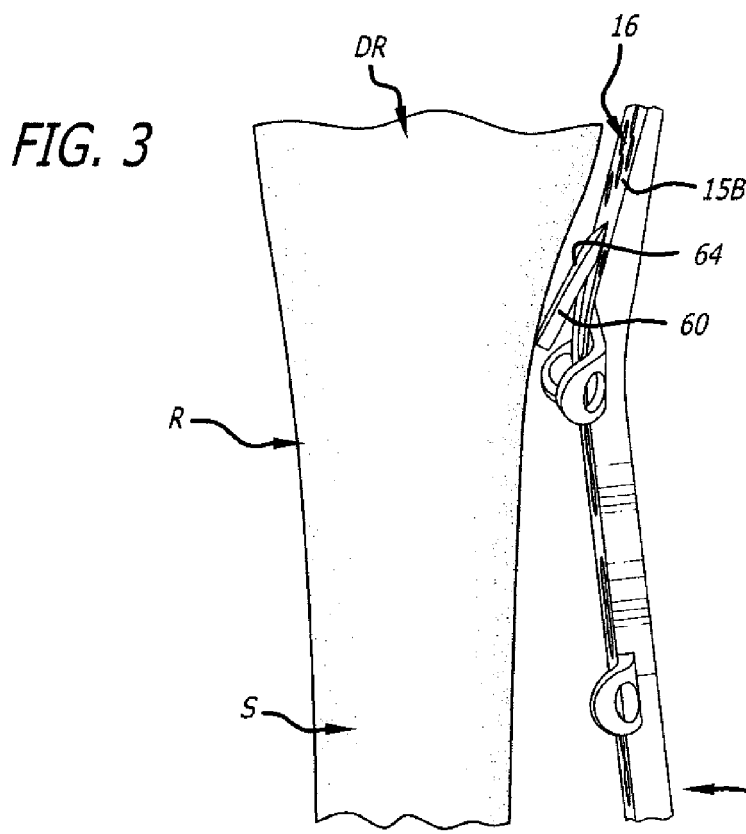
FIG. 3 is a side view of the bone fixation and reduction apparatus as depicted in FIG. 2, aligned for attachment with the radius and the distal radius, with the flex tab contacting at least one of a shaft of the radius proximate the fractured distal radius and the fractured distal radius, in accordance with the invention.
Figure 4:
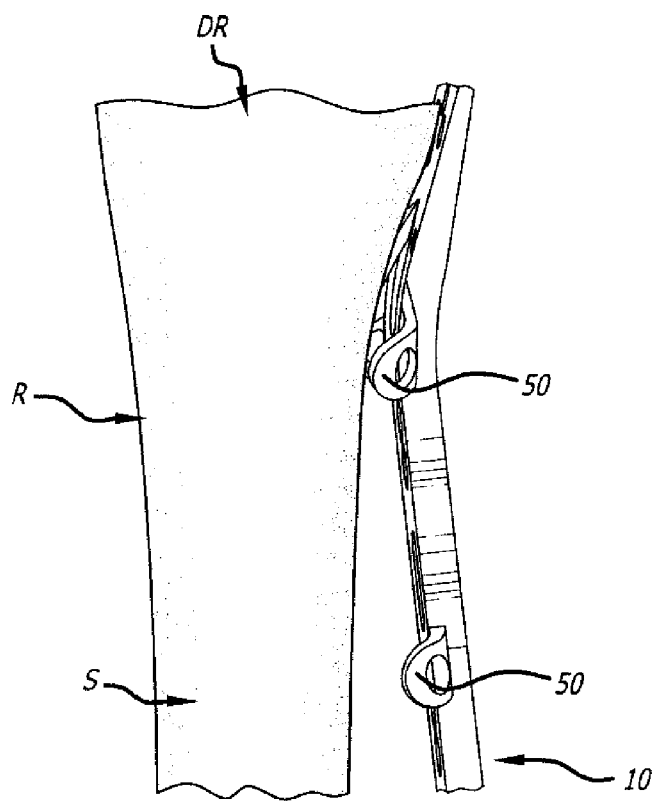
FIG. 4 is a side view of the bone fixation and reduction apparatus as depicted in FIG. 3, with the flex tab in contact with at least one of a shaft of the radius proximate the fractured distal radius and the fractured distal radius, a head portion in contact with the distal radius, and an elongated body portion projecting at an angle from the head portion, in accordance with the invention.
Figure 5:
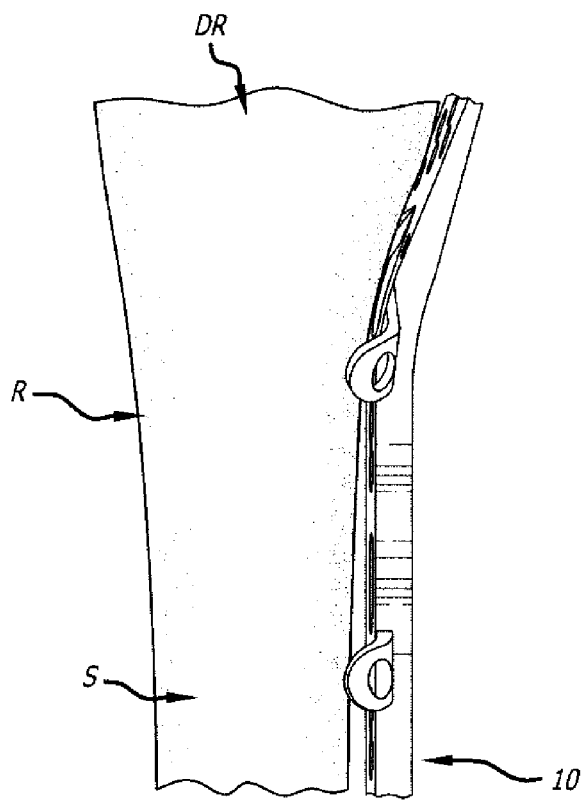
FIG. 5 is side view of the bone fixation and reduction apparatus as depicted in FIG. 4 with the flex tab in contact with at least one of a shaft of the radius proximate the fractured distal radius and the fractured distal radius, the head portion in contact with the distal radius, the elongated body portion pivoted into contact with the shaft of the radius, and alignment tabs projecting from portions of the perimeter of the apparatus, in accordance with the invention.
Figure 6:
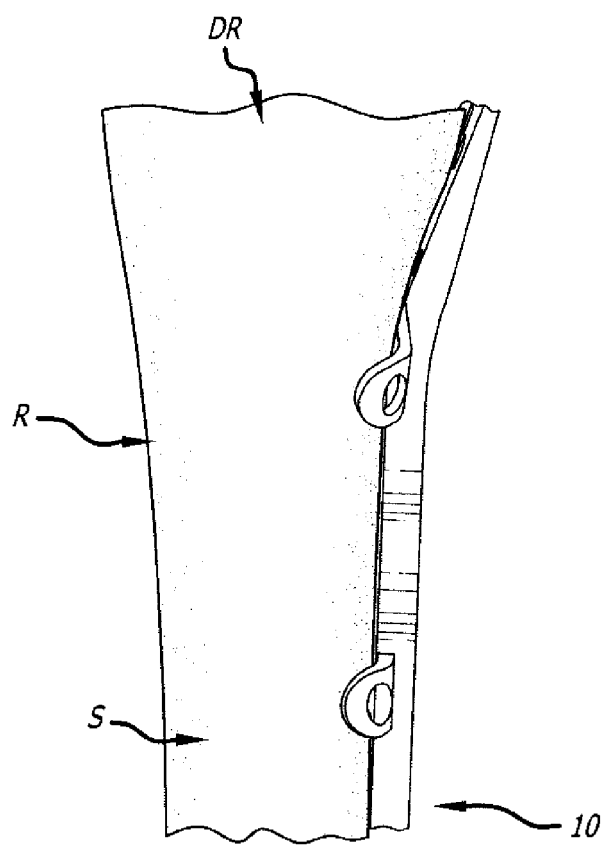
FIG. 6 is a side view of the bone fixation and reduction apparatus as depicted in FIG. 5, with the flex tab in contact with at least one of a shaft of the radius proximate the fractured distal radius and the fractured distal radius, the head portion in contact with the distal radius, the elongated body portion pivoted into contact with the shaft of the radius, and the alignment tabs pivoted into contact with the shaft of the radius.
Figure 7:
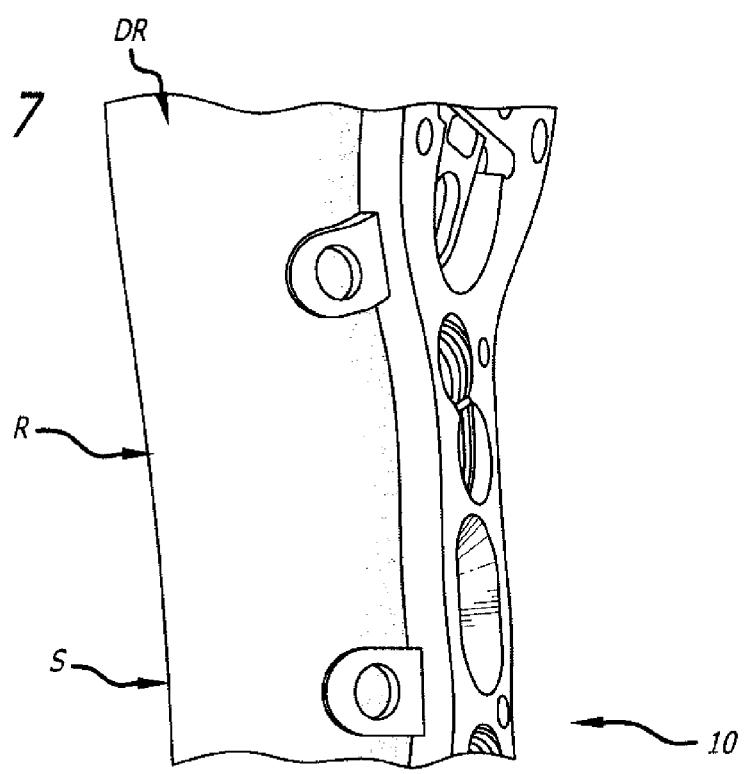
FIG. 7 is a front perspective view of the bone fixation and reduction apparatus as depicted in FIG. 6.
Figure 8:
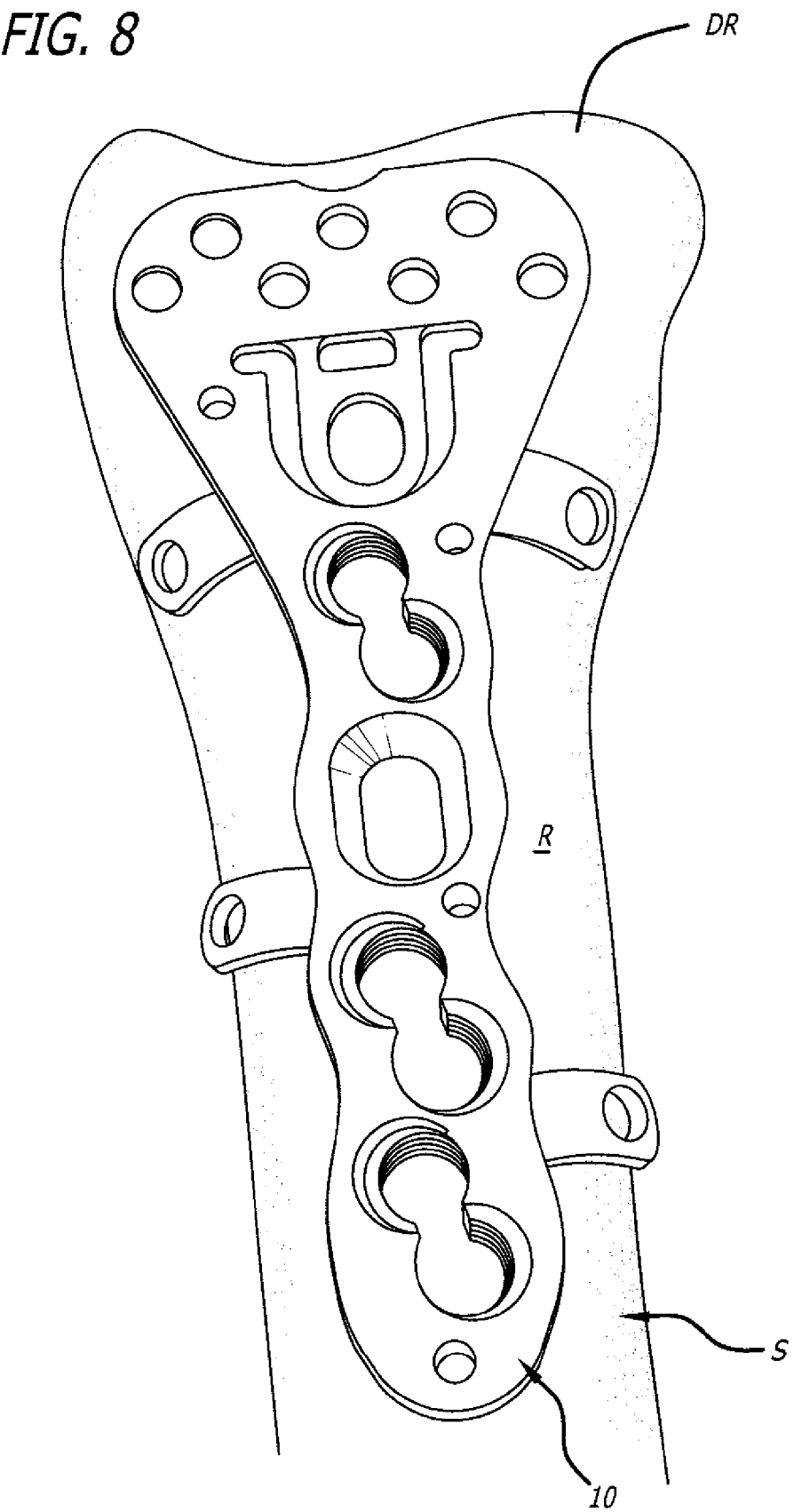
FIG. 8 is a front view of the bone fixation and reduction apparatus as depicted in FIG. 7.

FIGS. 1-16A depict positioning relative to and attachment of the bone plate 10 to the radius R. In FIGS. 2 and 3, the head portion 16 and the flex tab 60 (e.g., the lower surface 15B and the first surface 64 thereof) are brought into contact with the fractured distal radius DR. The head portion 16 can be contacted to a fragment of the fractured distal radius DR, and the flex tab 60 can be contacted to a portion of the fractured distal radius DR still attached to the radial shaft S. Alternately, the head portion 16 and the flex tab 60 can both be contacted to a fragment of the fractured distal radius DR. Alternately, the flex tab 60 can be attached to a portion of the shaft S of the radius R proximate the fractured distal radius DR. Either way, the flex tab 60 serves in exerting pressure on the radius R to serve in facilitating alignment of portions thereof.

In FIGS. 5-8, the remainder of the head portion 16 and the body portion 18 are brought into position with respect to the radius R. The alignment tabs 50 serve in guiding the bone plate 10 into position on the radius R. In doing so, the lower surface 15B at the head portion 16 and the body portion 18 is brought into engagement with the radius R. In doing so, the remainder of lower surface 15B at the head portion 16 (not already in contact therewith) is contacted to the fractured distal radius DR, and the lower surface 15B at the body portion 18 is contacted to portions of the radial shaft S and/or the fractured distal radius DR.

Figure 10:
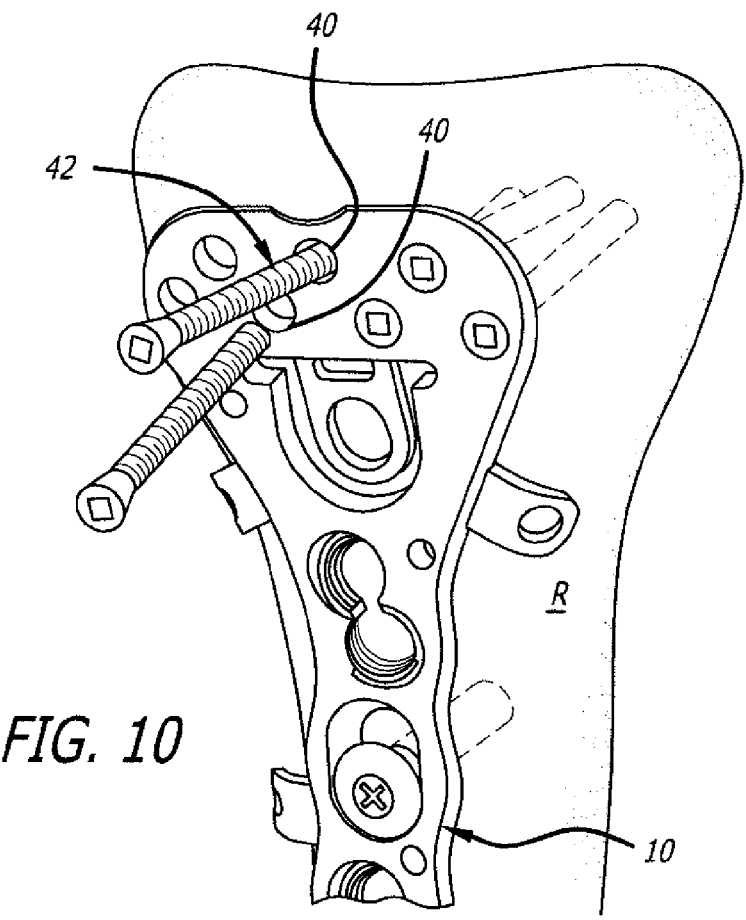
FIG. 10 is a front perspective view viewed from below the distal radius of the bone fixation and reduction apparatus in accordance with the invention, placed on the radius and distal radius, depicting an adjusting fastener inserted through an elongated aperture for adjusting a position of the bone fixation and reduction apparatus with respect to the radius, and fasteners being inserted through apertures in the head portion to attach the head portion to the distal radius.
Figure 11:
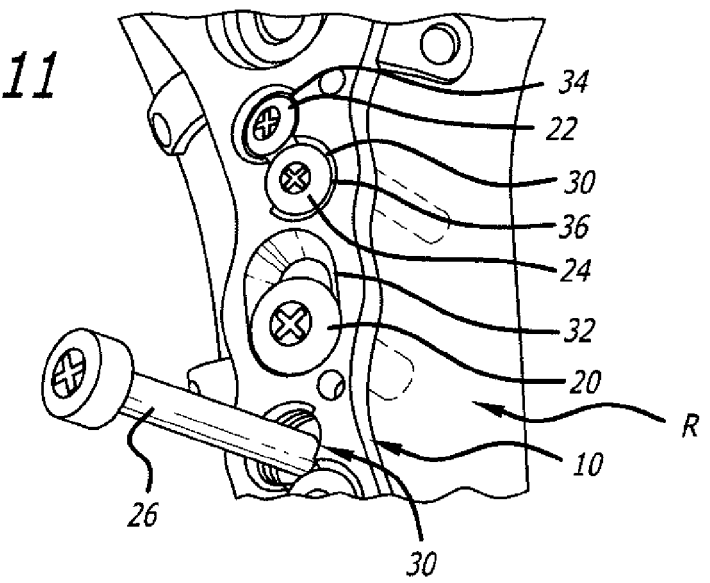
FIG. 11 is a front perspective view viewed from below the distal radius of the bone fixation and reduction apparatus in accordance with the invention, placed on the radius and distal radius, depicting an adjusting fastener inserted through an elongated aperture for adjusting a position of the bone fixation and reduction apparatus with respect to the radius, a fastener being inserted through an aperture in the elongated body portion to attach the elongated body portion to the radius, and a pair of fasteners inserted through a bi-directional aperture defined in the elongated body portion to attach the elongated body portion to the radius.
Figure 12:
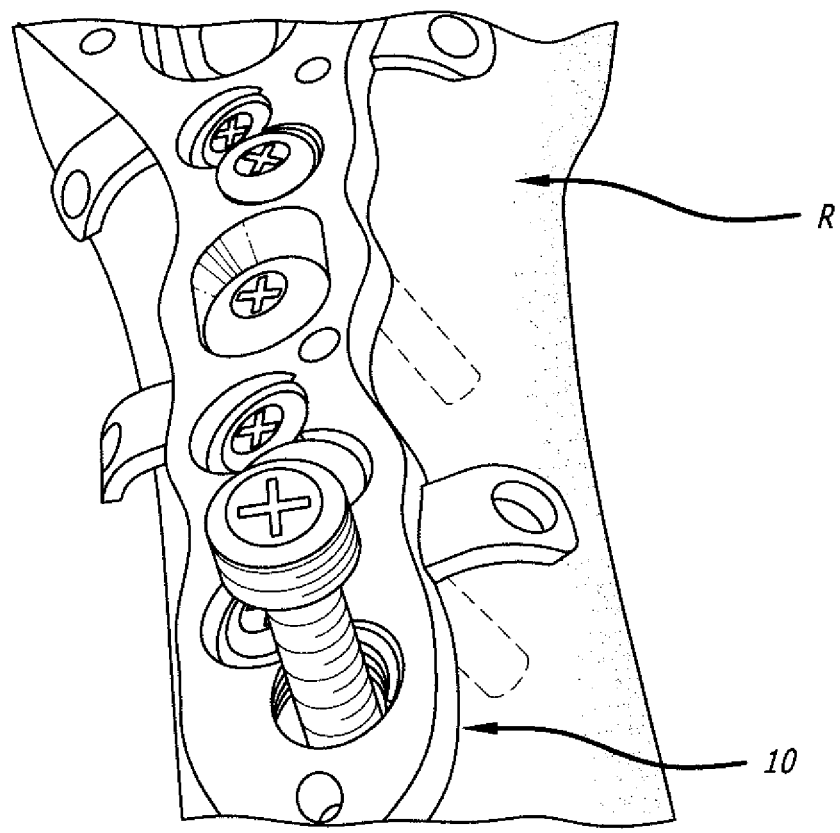
FIG. 12 is a front perspective view viewed from above the distal radius of the bone fixation and reduction apparatus in accordance with the invention, placed on the radius and distal radius, depicting an adjusting fastener inserted through an elongated aperture for adjusting a position of the bone fixation and reduction apparatus with respect to the radius, a fastener being inserted through an aperture in the elongated body portion to attach the elongated body portion to the radius, and a pair of fasteners inserted through a bi-directional aperture defined in the elongated body portion to attach the elongated body portion to the radius.
Figure 13:
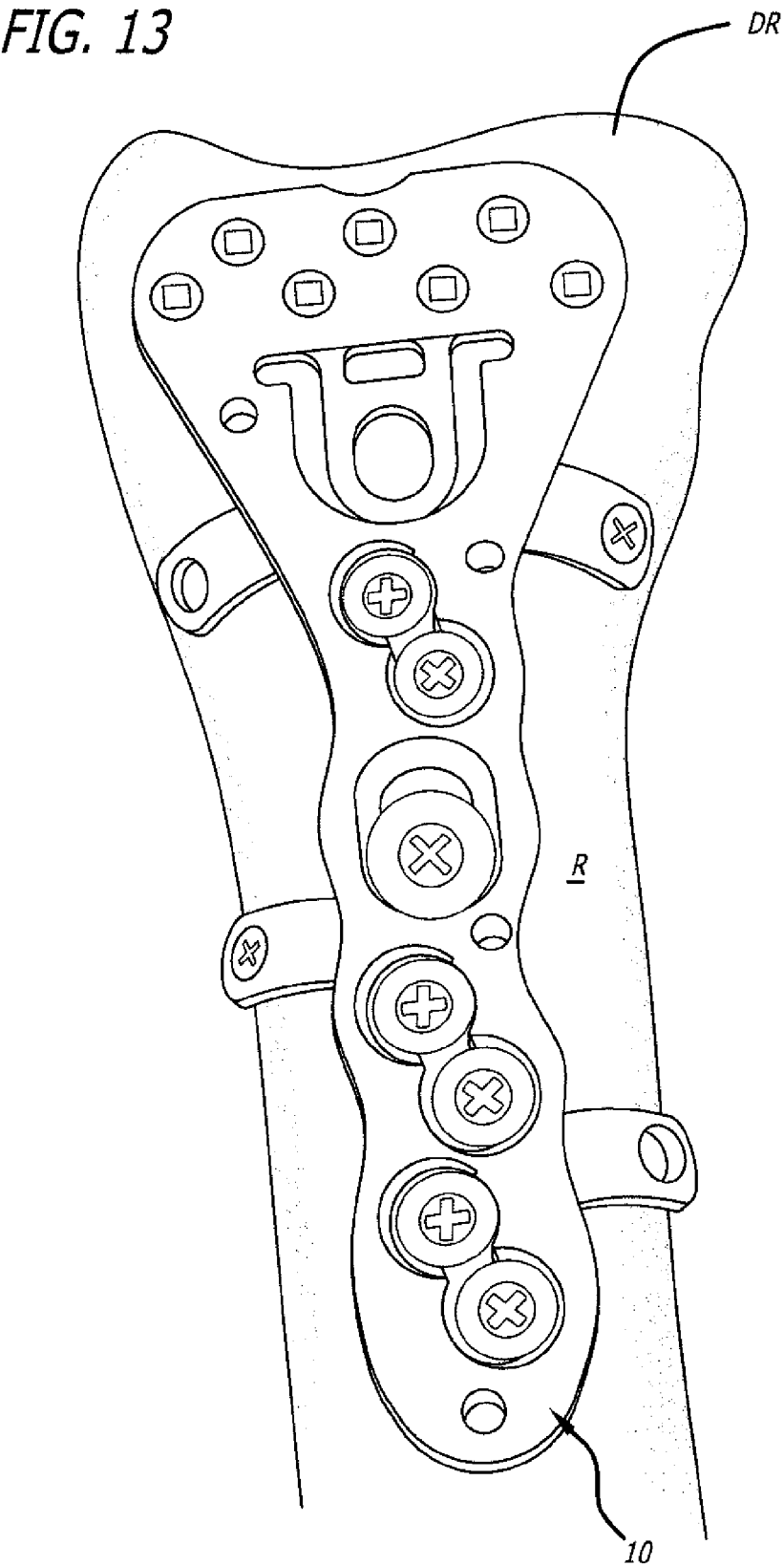
FIG. 13 is a front perspective view viewed from above the distal radius of the bone fixation and reduction apparatus in accordance with the invention with pairs of fasteners inserted through bi-directional apertures defined in the elongated body portion into the shaft portion of the radius, an adjusting fastener inserted through an elongated aperture for adjusting a position of the bone fixation and reduction apparatus with respect to the radius, and fasteners inserted through two of the adjustable alignment tabs into the shaft portion of the radius.
Figure 14:
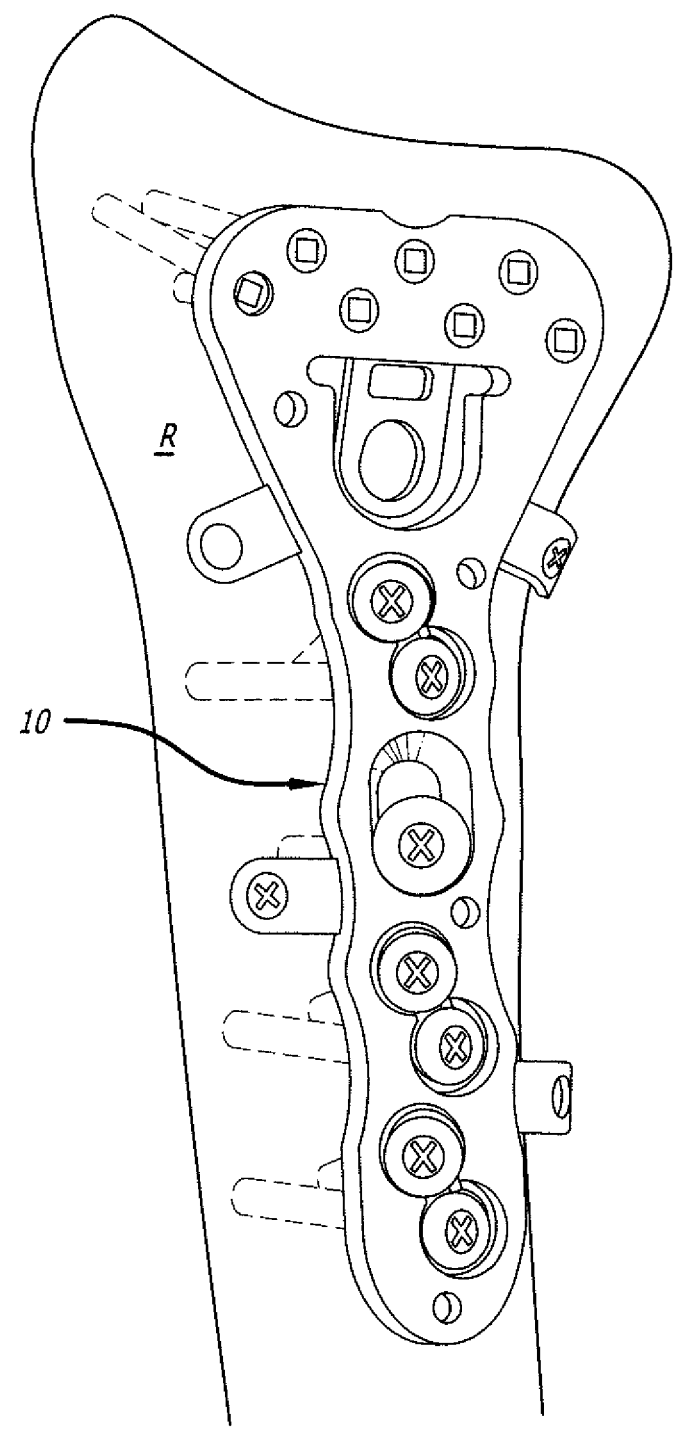
FIG. 14 is a front perspective view viewed from above the distal radius of the bone fixation and reduction apparatus in accordance with the invention, depicting the paths of fasteners inserted through bi-directional apertures into the shaft portion of the radius, an adjusting fastener inserted through an elongated aperture for adjusting a position of the bone fixation and reduction apparatus with respect to the radius, the paths of fasteners inserted through apertures defined in the head portion into the distal radius, and fasteners inserted through two of the adjustable alignment tabs into the shaft portion of the radius.
Figure 15:
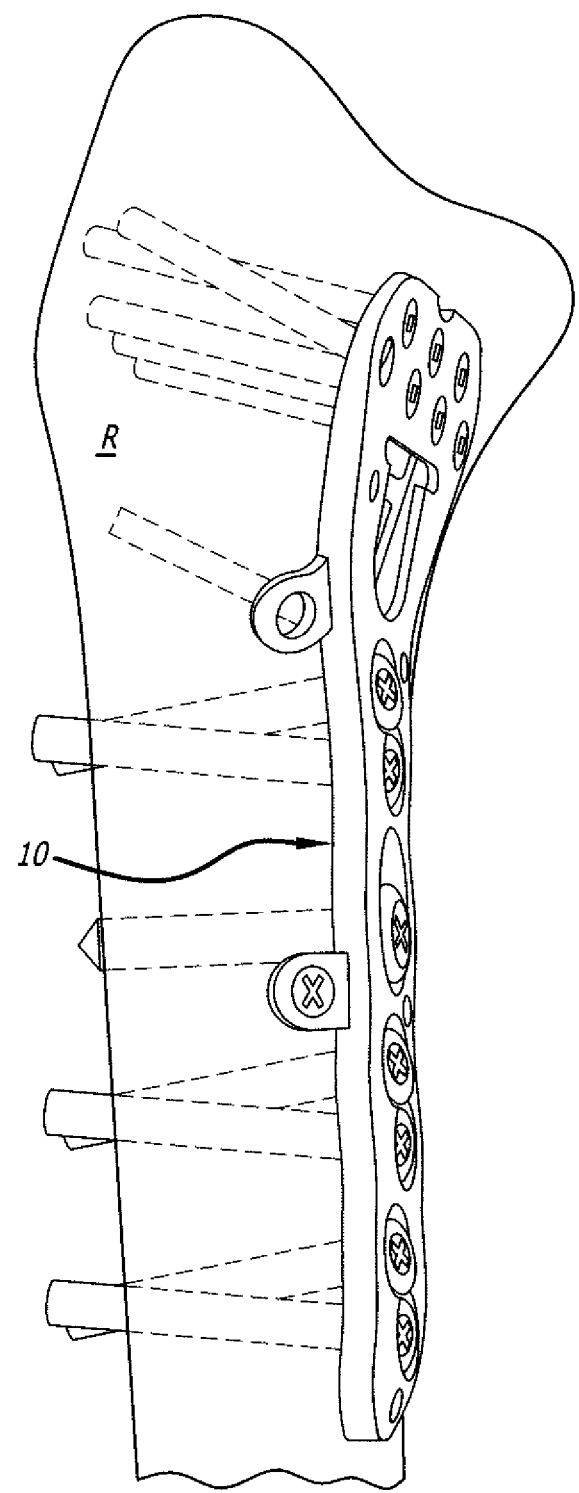
FIG. 15 is a side view of the bone fixation and reduction apparatus in accordance with the invention as depicted in FIG. 14.
Figure 19:
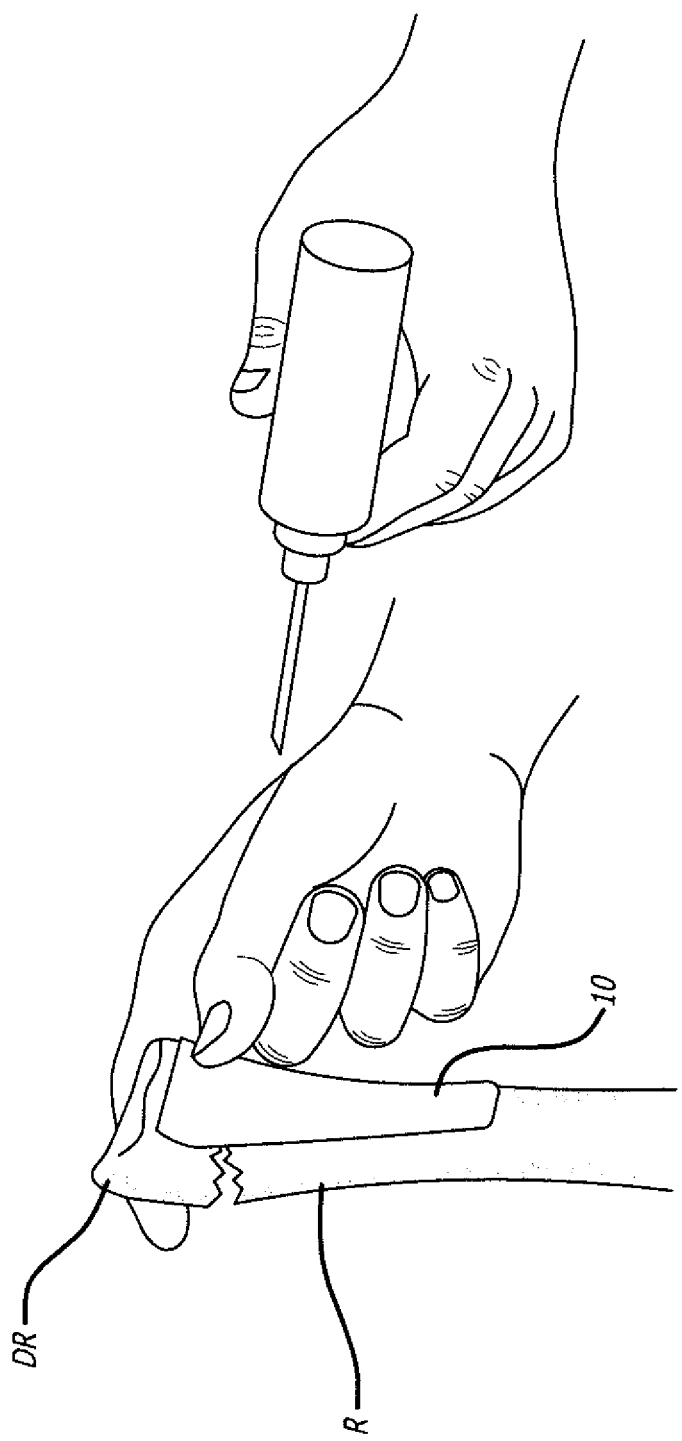
FIG. 19 is a front perspective view of a prior art method of reducing a fractured distal radius with a bone plate, depicting typical problems experienced by surgeons attempting to hold together fractured portions of a fractured distal radius, and a traditional bone plate with one hand, while attempting to hold a drill or another surgical tool with the other hand.
Figure 20:
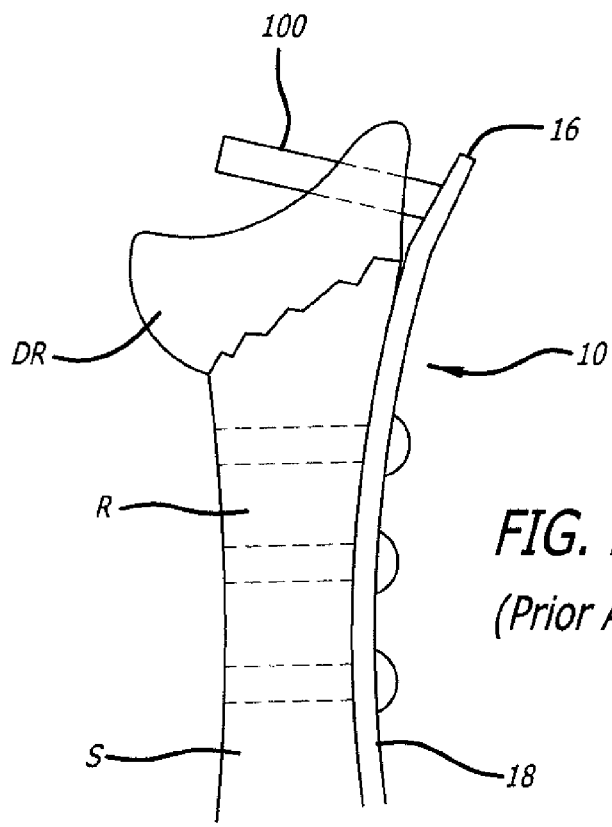
FIG. 20 is a prior art side view of an improperly reduced fractured distal radius obtained by using the traditional apparatus and method, wherein the fractured distal radius is improperly aligned with the proximal radius, thereby potentially resulting in a malunion, and a fastener potentially extending through the fractured distal radius into the tendons of the wrist.
Figure 21:
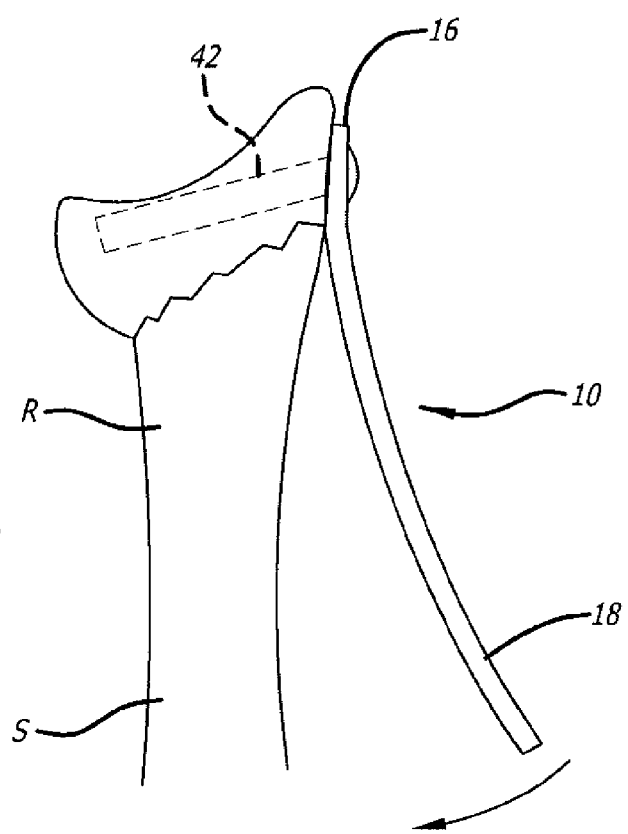
FIG. 21 is an illustrative side view depicting attachment of the head portion of a bone plate to a fractured distal radius, while pivoting the elongated body portion of the bone plate toward the shaft portion of the radius in an attempt to align the fractured distal radius with the proximal radius.
Figure 22:
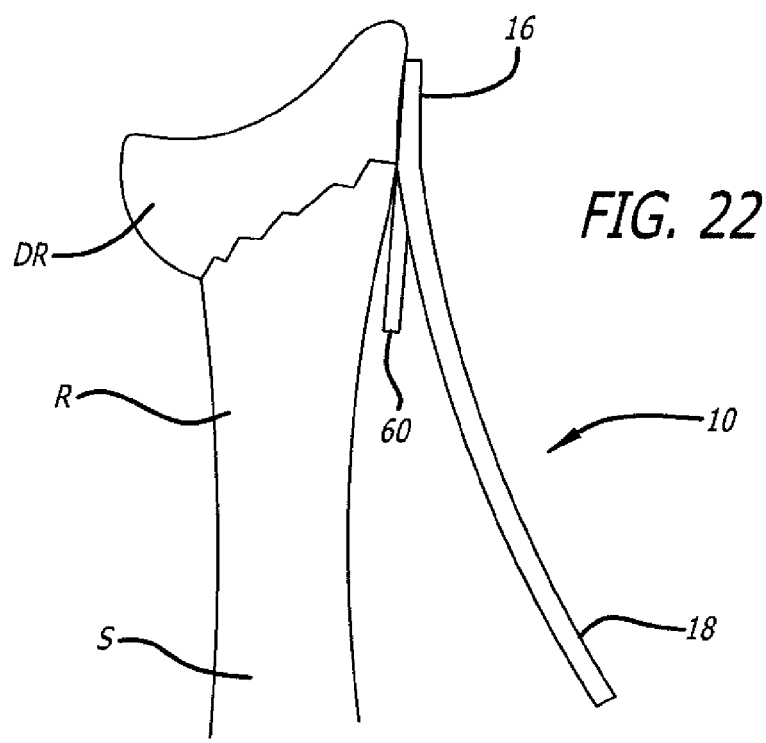
FIG. 22 is a side view depicting the method in accordance with the invention of reducing a fractured distal radius using the bone fixation and reduction apparatus in accordance with the invention, by placing the head of the apparatus against the fractured distal radius, and pivoting the flex tab toward at least one of a shaft of the radius proximate the fractured distal radius and the fractured distal radius.
Figure 23:
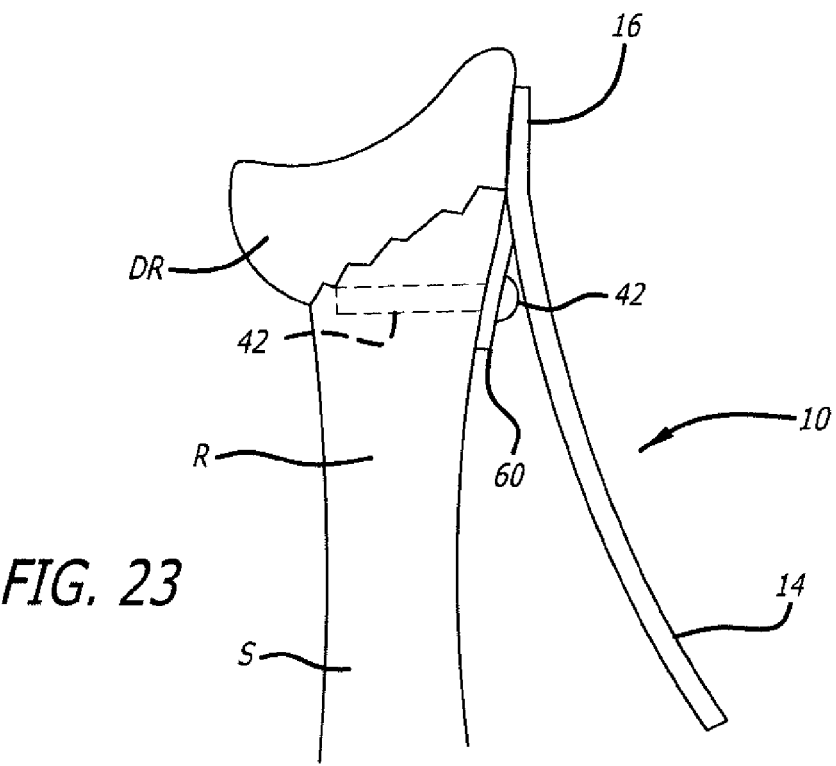
FIG. 23 is a side view of the method in accordance with the invention as depicted in FIG. 22, further depicting attaching the flex tab to at least one of a shaft of the radius proximate the fractured distal radius and the fractured distal radius with a fastener, thereby stabilizing the apparatus with respect to the radius, and freeing up one of the surgeon's hands.
Figure 24:
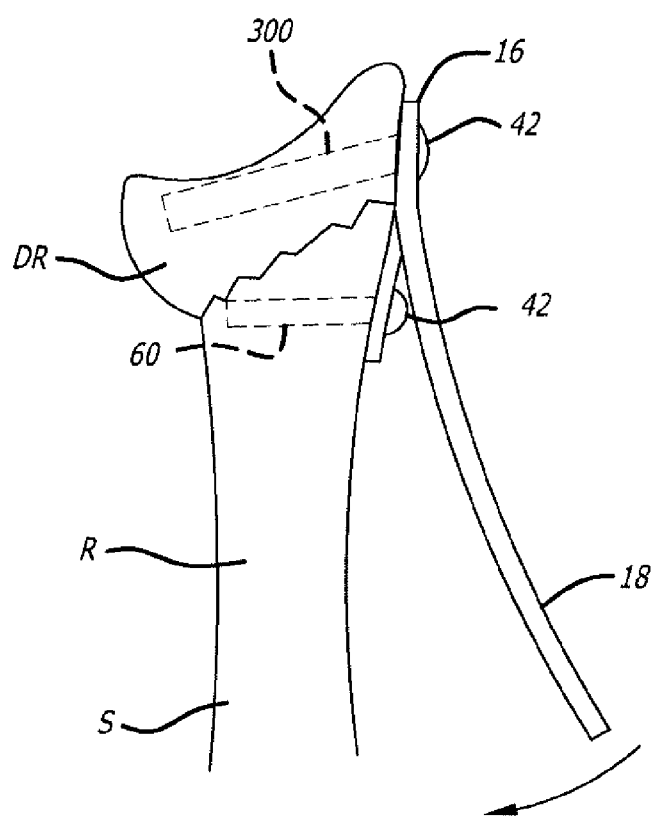
FIG. 24 is a side view of the method in accordance with the invention, as depicted in FIG. 23, further depicting attaching the head portion of the apparatus to the fractured distal radius with a fastener, and applying pressure to the elongated body portion, to pivot the elongated body portion toward the shaft of the radius, thereby aligning the fractured distal radius and the shaft of the radius.
Figure 25:
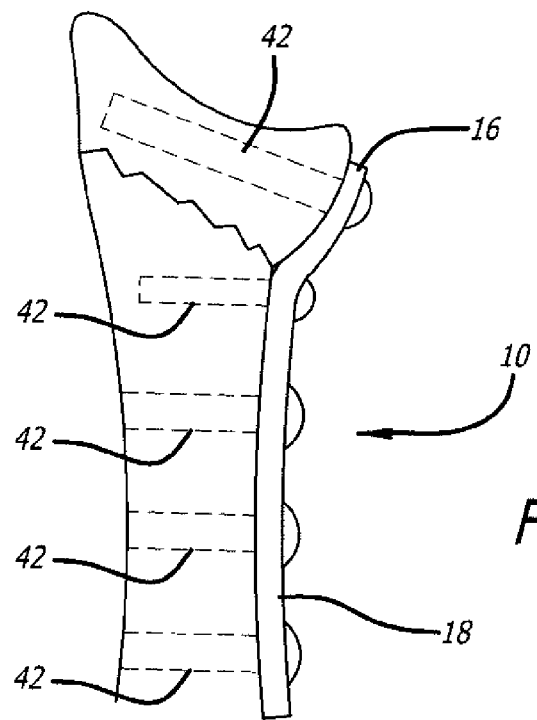
FIG. 25 is a side view of the method in accordance with the invention as depicted in FIG. 24, further depicting attachment of the elongated body portion, with fasteners, to the shaft portion of the radius.

In FIG. 9, one of the surgical pins 78 can be inserted through one of the apertures 76 and into the radius R to temporarily hold the bone plate 10 in position. Thereafter, the fastener 20 is received in the aperture 32 to attach the body portion 18 to the radius R. In FIG. 10, the fasteners 42 are inserted into the apertures 40 to attach the head portion 16 to the fractured distal radius DR, and in FIGS. 11 and 12, the fasteners 22, 24, and 26 are inserted into the apertures 30 and 32 to attach the body portion 18 to portions of the radial shaft S and/or the fractured distal radius DR. As depicted in FIGS. 13-15, fasteners (such as fasteners 42) can be inserted through the apertures 52 formed in the alignment tabs 50 and into portions of the radial shaft S and/or the fractured distal radius DR to also attach the bone plate 10 to the radius R.

FIGS. 13-15 depicted the bone plate 10 attached to the radius R. As discussed above, the bone plate 10 facilitates reduction and repair of the fractured distal radius DR to aid healing thereof.

As discussed above, the apertures 52 of the alignment tabs (or fixation legs) 50 can be used to receive fasteners (such as the fasteners 42) therein. In doing so, the fasteners (such as the fasters 42) can be used in attaching the bone plate 10 to the radius R. To illustrate, the fasteners can be inserted through the apertures 52 formed in the alignment tabs (or fixation legs) 50 and into portions of the radial shaft S and/or the fractured distal radius DR to also attach the bone plate 10 to the radius R.

As depicted in FIGS. 16A and 16B, the fasteners received through the apertures 52 in the alignment tabs (or fixation legs) 50 depicted therein can be oriented at various angles with respect to the body portion of the bone plate. The angles at which the fasteners are oriented with respect to the body portion depend on the orientation of the alignment tabs (or fixation legs) 50 and/or the angles of the apertures through the alignment tabs (or fixation legs) 50.

The alignment tabs (or fixation legs) depicted in FIGS. 16A and 16B can be formed of material which may be as thick as or thinner than the bone plate from which they depend from. Furthermore, at least one aperture (such as one of the apertures 52 discussed above or apertures 100 depicted in FIG. 16A) can be formed in each of the alignment tabs (or fixation legs) 50.

The alignment tabs (or fixation legs) 50 can be bent in various directions (such as directions A-A' depicted in FIG. 16A) with respect to the body portion. Furthermore, the angles of the apertures through the alignment tabs (or fixation legs) 50 can be varied. Thus, depending on the orientation of the alignment tabs (or fixation legs) 50 and the angles of the apertures 52 through the alignment tabs (or fixation legs) 50, the fasteners inserted through the apertures can be varied. For example, as depicted in FIGS. 15 and 16A, the fasteners can be oriented at acute angles less than 45 degrees with respect to the lower surface of the body portion of the bone plate.

A preferred method for fixation and reduction of a fractured distal radius DR, as broadly embodied in FIGS. 21-25 includes: utilizing the bone plate 10, including: the elongated body portion 18 adapted for attachment to the shaft portion S of the radius R, the elongated body portion 18 defining a longitudinal axis extending substantially parallel to a shaft portion of the radius R; the head portion 16 connected to the elongated body portion 18, and projecting therefrom at a first angle respect to the longitudinal axis, the head portion 16 being adapted for attachment to the fractured distal radius DR; at least one of the alignment tabs 50 projecting from the perimeter P of at least one of the head portion 16 and the elongated body portion 18; and the flex tab 60 connected to the surface of the opening 62 defined in the head portion 16 and extending substantially parallel to the longitudinal axis, adapted to be pivoted into contact with, and to be attached to shaft portion of the radius R proximate the fractured distal radius DR; aligning the head portion 16 on the fractured distal radius DR with at least one of the alignment tabs 50, such that the elongated body portion 18 projects away from the shaft portion S of the radius R at an angle corresponding to the first angle; pivoting the flex tab 60 into contact with the shaft portion S of the radius R proximate the fractured distal radius DR; attaching the flex tab 60 to the shaft portion S of the radius R proximate the fractured distal radius DR; attaching the head portion to the fractured distal radius DR with a fastener 42; attaching pressure to the elongated body portion 18 to bring the elongated body portion into contact with the shaft portion of the radius, thereby aligning the fractured distal radius DR with the shaft S of the radius R; and attaching the elongated body portion 18 with a fastener 42 to the shaft S of the radius R.

As broadly embodied herein, a preferred method for fixation and reduction of a malformed distal radius, resulting from a malunion of the distal radius DR and the shaft S of the radius R, includes substantially all of the above steps used in the method for fixation and reduction of a fractured distal radius, but also includes a step, prior to aligning the bone plate 10 with the radius R of cutting the malformed distal radius DR with respect to the shaft S of the radius R.

In summary, the bone plate 10 facilitates reduction and repair of bone fractures and malunions (such as a fractured or malformed distal radius).

Other embodiments of the invention will be apparent to those skilled in the art from consideration of the specification and practice of the invention disclosed herein. Accordingly, it is intended that the specification and disclosed embodiments and methods be considered as exemplary only, with the true scope and spirit of the invention being indicated by the following claims.

I claim:

1. An apparatus for fixation and reduction of a fractured distal portion of a bone, comprising:
a bone plate comprising:
an elongated body portion adapted for attachment to a shaft portion of the bone, said elongated body portion defining a longitudinal axis extending substantially parallel to the shaft portion of the bone;
a head portion connected to said elongated body portion, and projecting therefrom at a first angle with respect to the longitudinal axis, said head portion adapted for attachment to the fractured distal portion of the bone;
at least one alignment tab projecting from a perimeter of at least one of said head portion and said elongated body portion; and
a flex tab connected to a surface of an opening defined in said head portion and extending substantially parallel to the longitudinal axis, adapted to be pivoted into contact with, and to be attached to, at least one of the shaft portion of the bone proximate the fractured distal portion of the bone and the fractured distal portion of the bone.

2. The apparatus in accordance with claim 1, further comprising at least one fastener adapted to be inserted through at least one aperture defined in said elongated body portion for attaching said elongated body portion to the shaft portion of the bone.

3. The apparatus in accordance with claim 2, wherein said at least one fastener is adapted to be inserted through at least one elongated aperture defined in said elongated body portion, said elongated aperture defining an elongated aperture axis, wherein said bone plate is movable along said elongated aperture axis relative to the bone and relative to said at least one fastener.

4. The apparatus in accordance with claim 1, further comprising at least one bidirectional aperture defined in at least one of said elongated body portion and said head portion, adapted to receive two fasteners therethrough.

5. The apparatus in accordance with claim 1, wherein a first of said at least one alignment tab projecting from the perimeter of said head portion has a first aperture defined therein adapted to receive therethrough a first fastener in a first line, in a plane substantially perpendicular to the longitudinal axis, the first line extending from said first aperture through a center of the distal portion of the bone.

6. The apparatus in accordance with claim 5, wherein a second of said at least one alignment tab projecting from the perimeter of said head portion has a second aperture defined therein adapted to receive therethrough a second fastener in a second line, in the plane substantially perpendicular to the longitudinal axis, the second line extending from said second aperture through the center of the distal portion of the bone, and crossing the first line.

7. The apparatus in accordance with claim 1, wherein said at least one flex tab, after attachment to said at least one of the shaft portion proximate the fractured distal portion of the bone and the fractured distal portion of the bone, is adapted to stabilize said bone plate with respect to the bone.

8. The apparatus in accordance with claim 1, further comprising at least one surgical pin adapted to be temporarily inserted through at least one aperture in at least one of said head portion and said elongated body portion, said surgical pin being adapted to position said bone plate relative to the bone.

9. The apparatus in accordance with claim 1, further comprising at least one fastener adapted to be inserted through at least one aperture defined in said head portion for attaching said head portion to the fractured distal portion of the bone.

10. The apparatus in accordance with claim 1, further comprising a fastener adapted to be inserted through an aperture defined in said flex tab for attaching said flex tab to said at least one of the shaft portion of the bone proximate the fractured distal portion of the bone and the fractured distal portion of the bone.

11. The apparatus in accordance with claim 1, wherein said at least one alignment tab is adapted to position said bone plate on the bone.

12. The apparatus in accordance with claim 11, wherein said at least one alignment tab projecting from said head portion is further adapted to attach together comminuted fractured portions of the fractured distal end portion of the bone.

13. The apparatus in accordance with claim 11, wherein said at least one alignment tab is flexible through a range of acute angles with respect to at least one of said elongated body portion and said head portion.

14. The apparatus in accordance with claim 13, further comprising a fastener adapted to be inserted through an aperture defined in said at least one alignment tab oriented in the range of acute angles, for attaching said at least one alignment tab to the bone.

15. The apparatus in accordance with claim 1, wherein said bone plate is further adapted for fixation and reduction of a malunion of a distal portion of the bone.

16. The apparatus in accordance with claim 1, wherein said bone plate is adapted for fixation and reduction of at least one of a fractured distal radius, a fractured distal tibia, a fractured distal femur, a fractured proximal humerus, a fractured metacarpal, a fractured proximal phalange, a malunion of a distal radius, a malunion of a distal tibia, a malunion of a distal femur, a malunion of a proximal humerus, a malunion of a metacarpal, and a malunion of a proximal phalange.

17. A method for fixation and reduction of a fractured distal portion of a bone, comprising:
utilizing a bone plate comprising:
an elongated body portion adapted for attachment to a shaft portion of the bone, said elongated body portion defining a longitudinal axis extending substantially parallel to the shaft portion of the bone;
a head portion connected to said elongated body portion, and projecting therefrom at a first angle with respect to the longitudinal axis, said head portion adapted for attachment to the fractured distal portion of the bone;
at least one alignment tab projecting from a perimeter of at least one of said head portion and said elongated body portion; and
a flex tab connected to a surface of an opening defined in said head portion and extending substantially parallel to the longitudinal axis, having an inner surface adapted to be pivoted into contact with, and to be attached to, at least one of the shaft portion of the bone proximate the fractured distal portion of the bone and the fractured distal portion of the bone;
aligning said head portion on the fractured distal portion of the bone, such that said elongated body portion projects away from the shaft portion of the bone at an angle corresponding to the first angle;
pivoting said flex tab into contact with the at least one of the shaft portion of the bone proximate the fractured distal portion of the bone and the fractured distal portion of the bone;
attaching said flex tab to the at least one of the shaft portion of the bone proximate the fractured distal portion of the bone and the fractured distal portion of the bone;
attaching said at least one alignment tab to the bone;
attaching said head portion to the fractured distal portion of the bone;
applying pressure to said elongated body portion to bring said elongated body portion into contact with the shaft portion of the bone; and
attaching said elongated body portion to the shaft portion of the bone.

18. The method in accordance with claim 17, wherein applying pressure to said elongated body portion moves the fractured distal portion of the bone into alignment with the shaft portion of the bone.

19. The method in accordance with claim 17, wherein attaching said flex tab to said at least one of the shaft portion proximate the fractured distal portion of the bone and the fractured distal portion of the bone stabilizes said bone plate with respect to the bone.

20. A method for fixation and reduction of a malformed distal portion of a bone, comprising:
utilizing a bone plate comprising:
an elongated body portion adapted for attachment to a shaft portion of the bone, said elongated body portion defining a longitudinal axis extending substantially parallel to the shaft portion of the bone;
a head portion connected to said elongated body portion, and projecting therefrom at a first angle with respect to the longitudinal axis, said head portion adapted for attachment to the malformed distal portion of the bone;
at least one alignment tab projecting from a perimeter of at least one of said head portion and said elongated body portion; and
a flex tab connected to a surface of an opening defined in said head portion and extending substantially parallel to the longitudinal axis, adapted to be pivoted into contact with, and to be attached to, at least one of the shaft portion of the bone proximate the malformed distal portion of the bone and the malformed distal portion of the bone;
cutting the malformed distal portion of the bone with respect to the shaft portion of the bone proximate the malformed distal portion of the bone;
aligning said head portion on the malformed distal portion of the bone, such that said elongated body portion projects away from the shaft portion of the bone at an angle corresponding to the first angle;

pivoting said flex tab into contact with the at least one of the surface of the shaft portion of the bone proximate the malformed distal portion of the bone and the malformed distal portion of the bone;

attaching said flex tab to the at least one of the shaft portion of the bone proximate the malformed distal portion of the bone and the malformed distal portion of the bone;

attaching said at least one alignment tab to the bone;

attaching said head portion to the malformed distal portion of the bone, such that said elongated body portion projects away from the shaft portion of the bone at the angle corresponding to the first angle;

applying pressure to said elongated body portion to bring said elongated body portion into contact with the shaft portion of the bone; and attaching said elongated body portion to the shaft portion of the bone.

* * * * *